(12) United States Patent
Amit et al.

(10) Patent No.: US 8,354,277 B2
(45) Date of Patent: Jan. 15, 2013

(54) ISOLATED PRIMATE EMBRYONIC CELLS DERIVED FROM EXTENDED BLASTOCYSTS

(75) Inventors: Michal Amit, Misgav (IL); Joseph Itskovitz-Eldor, Haifa (IL)

(73) Assignee: Technion Research & Development Foundation Ltd., Haifa (IL)

( * ) Notice: Subject to any disclaimer, the term of this patent is extended or adjusted under 35 U.S.C. 154(b) by 0 days.

(21) Appl. No.: 11/665,248

(22) PCT Filed: Oct. 11, 2005

(86) PCT No.: PCT/IL2005/001074
§ 371 (c)(1),
(2), (4) Date: Apr. 12, 2007

(87) PCT Pub. No.: WO2006/040763
PCT Pub. Date: Apr. 20, 2006

(65) Prior Publication Data
US 2009/0196860 A1 Aug. 6, 2009

Related U.S. Application Data

(60) Provisional application No. 60/617,045, filed on Oct. 12, 2004.

(51) Int. Cl.
*C12N 15/00* (2006.01)
(52) U.S. Cl. .................. 435/373; 435/366; 435/378
(58) Field of Classification Search ............... None
See application file for complete search history.

(56) References Cited

U.S. PATENT DOCUMENTS

| | | | |
|---|---|---|---|
| 5,851,832 A | 12/1998 | Weiss et al. | |
| 6,280,718 B1 | 8/2001 | Kaufman et al. | |
| 7,267,981 B2 | 9/2007 | Amit et al. | |
| 7,326,572 B2 * | 2/2008 | Fisk et al. | 435/377 |
| 7,510,876 B2 * | 3/2009 | D'Amour et al. | 435/366 |
| 2002/0188963 A1 * | 12/2002 | Loring | 800/14 |

FOREIGN PATENT DOCUMENTS
WO   WO 2005/080551   9/2005

OTHER PUBLICATIONS

Brook et al. The origin and efficient derivatioln of embryonic stem cells in the mouse. Proceed. Natl. Acad. Sci. (USA), 1997, vol. 94, pp. 5709-5712.*
Luckett. The development of primordial and definitive amniotic cavities in early rhesus monkey and human embryos. American J. Anatomy, 1975, vol. 144, pp. 149-168.*
Turner et al. /the invlfuence of Vero cell culture on human embryo development and chorionic gonadotrophin production in vitro. Human Reproduction, 1996, vol. 11, pp. 1966-1974.*
D'Amour et al. Efficient differentiation of human embryonic stem cells to definitive endoderm. Nature Biotech., 2005, vol. 23, pp. 1534-1541.*
Bigdeli et al. Adaptation of human embryonic stem cells to feeder-free and matrix-free culture conditions directly on plastic surfaces. J. Biotechnology, 2008, vol. 133, pp. 146-153.*
Strelchenko et al. Embryonic Stem Cells from Morula. Methods in Enzymology, 2006, vol. 418, pp. 93-108.*
Vallier et al. Activin/Nodal signalling maintains pluripotency by controlling Nanog expression. Development, 2009, vol. 136, pp. 1339-1349.*
Vallier et al. Ibid. Supplementary information, Development, 2009, vol. 136.*
Amit et al. "Clonally Derived Human Embryonic Stem Cell Lines Maintain Pluripotency and Proliferative Potential for Prolonged Periods of Culture", Developmental Biology, 227: 271-278, 2000.
Assady et al. "Insulin Production by Human Embryonic Stem Cells", Diabetes, 50(8): 1591-1697, 2001.
Eiges et al. "Establishment of Human Embryonic Stem Cell-Transfected Clones Carrying a Marker for Undifferentiated Cells", Current Biology, 11: 514-518, 2001.
Evans et al. "Pluripotent Cells Grown Directly From Normal Mouse Embryos", Cancer Surveys, 2(1): 185-207, 1983.
Hawley et al. "The HOX11 Homeobox-Containing Gene of Human Leukemia Immortalizes Murine Hematopoietic Precursors", Oncogene, 9: 1-12, 1994.
Itskovitz-Eldor et al. "Differentiation of Human Embryonic Stem Cells Into Embryoid Bodies Comprising the Three Embryonic Germ Layers", Molecular Medicine, 6(2): 88-95, 2000.
Lake et al. "Reversible Programming of Pluripotent Cell Differentiation", Journal of Cell Science, 113: 555-566, 2000.
Paquin et al. "Oxytocin Induces Differentiation of P19 Embryonic Stem Cells to Cardiomyocytes", Proc. Natl. Acad. Sci. USA, 99(14): 9550-9555, 2002.
Rathjen et al. "Formation of a Primitive Ectoderm Like Cell Population, EPL Cells, From ES Cells in Response to Biologically Derived Factors", Journal of Cell Science, 112: 601-612, 1999.
Reubinoff et al. "Embryonic Stemm Cell Lines From Human Blastocysts: Somatic Differentiation In Vitro", Nature Biotechnology, 18: 399-404, 2000.
Reubinoff et al. "Neural Progenitors From Human Embryonic Stem Cells", Nature Biotechnology, 19: 1134-1140, 2001.
Richards et al. "Human Feeders Support Prolonged Undifferentiated Growth of Human Inner Cell Masses and Embryonic Stem Cells", Nature Biotechnology, 20: 933-936, 2002.
Schuldiner et al. "Effects of Eight Growth Factors on the Differentiation of Cells Derived From Human Embryonic Stem Cells", Proc. Natl. Acad. Sci. USA, 97(21): 11307-11312, 2000.
Schuldiner et al. "Selective Ablation of Human Embryonic Stem Cells Expressing a 'Suicide' Gene", Stem Cells, 21: 257-265, 2003.
Stojkovic et al. "Derivation of Human Embryonic Stem Cells From Day-8 Blastocysts Recovered After Three-Step in Vitro Culture", Stem Cells, 22(5): 790-797, 2004. p.792, 1-h col., § 3.
Stojkovic et al. "Derivation, Growth and Applications of Human Embryonic Stem Cells", Reproduction, 128(3): 259-267, 2004. Fig. 2.
Thomson et al. "Embryonic Stem Cell Lines Derived From Human Blastocysts", Science, 282: 1145-1147, 1998.

(Continued)

*Primary Examiner* — Deborah Crouch

(57) ABSTRACT

An isolated primate embryonic cell is provided as well as cell cultures and cell lines derived therefrom. Also provided are methods of generating and using such cells.

36 Claims, 19 Drawing Sheets

OTHER PUBLICATIONS

Wei et al. "Abolition of Cyclin-Dependent Kinase Inhibitor P16[Ink4a] and P21[Cip 1/Waf1] Functions Permits Ras-Induced Anchorage-Independent Growth in Telomerase-Immortalized Human Fibroblasts", Molecular and Cellular Biology, 23(8): 2859-2870, 2003.

Weiss "Embryonic Stem Cells and Hematopoietic Stem Cell Biology", Hematology/Oncology Clinics of North America, 11(6): 1185-1198, 1997.

Xu et al. "Feeder-Free Growth of Undifferentiated Human Embryonic Stem Cells", Nature Biotechnology, 19: 971-974, 2001.

Slukvin et al. "Development of Lymphohematopoietic Progenitors During Human Embryonic Stem (HES) Cell Differentiation on OP9 Stromal Cells", Blood, 104(11/Part 1): 763A, 2004. Abstract. & 46th Annual Meeting of the American Society of-Hematology, San Diego, CA, USA, Dec. 4-7, 2004.

Wei et al. "Abolition of Cyclin-Dependent Kinase Inhibitor P16[Ink4a] and P21[Cip1/Waf1] Functions Permits Ras-Induced Anchorage-Independent Growth in Telomerase-Immortalized Human Fibroblasts", Molecular and Cellular Biology, 23(8): 2859-2870, 2003.

Thomson et al. "Isolation of a Private Embryonic Stem Cell Line", Proc. Natl. Acad. Sci. USA, 92: 7844-7848, Aug. 1995.

International Preliminary Report on Patentability Dated Apr. 26, 2007 From the International Bureau of WIPO Re.: Application No. PCT/IL2005/001074.

International Search Report and the Written Opinion Dated Jun. 21, 2006 From the International Searching Authority Re.: Application No. PCT/IL2005/001074.

International Search Report Dated Jun. 21, 2006 From the International Searching Authority Re.: Application No. PCT/IL2005/001074.

Written Opinion Dated Jun. 21, 2006 From the International Searching Authority Re.: Application No. PCT/IL2005/001074.

Communication Pursuant to Article 96(2) EPC Dated Aug. 10, 2007 From the European Patent Office Re.: Application No. 05796543.6.

Communication Pursuant to Article 96(2) EPC Dated Jun. 17, 2010 From the European Patent Office Re.: Application No. 05796543.6.

Vogel "Researchers Get Green Light for Work on Stem Cells", Science, XP001539915, 289(5484): 1442-1443, Sep. 1, 2000.

Vogel "Wisconsin to Distribute Embryonic Cell Lines", Science, XP001539914, 287(5455): 948-949, Feb. 11, 2000.

Response Dated Aug. 10, 2010 to Office Action of Dec. 10, 2009 From the Israel Patent Office Re.: Application No. 182516.

Barberi et al. "Derivation of Engraftable Skeletal Myoblasts From Human Embryonic Stem Cells", Nature Medicine, 13(5): 642-648, May 2007.

Office Action Dated Dec. 21, 2010 From the Israel Patent Office Re.: Application No. 182516 and Its Translation Into English.

Rodaway et al. "Mesendoderm: An Ancient Germ Layer?", Cell, 105(2): 169-172, Apr. 20, 2011.

Technau et al. "Origin and Evolution of Endoderm and Mesoderm", International Journal of Developmental Biology, 47: 531-539, 2003.

* cited by examiner

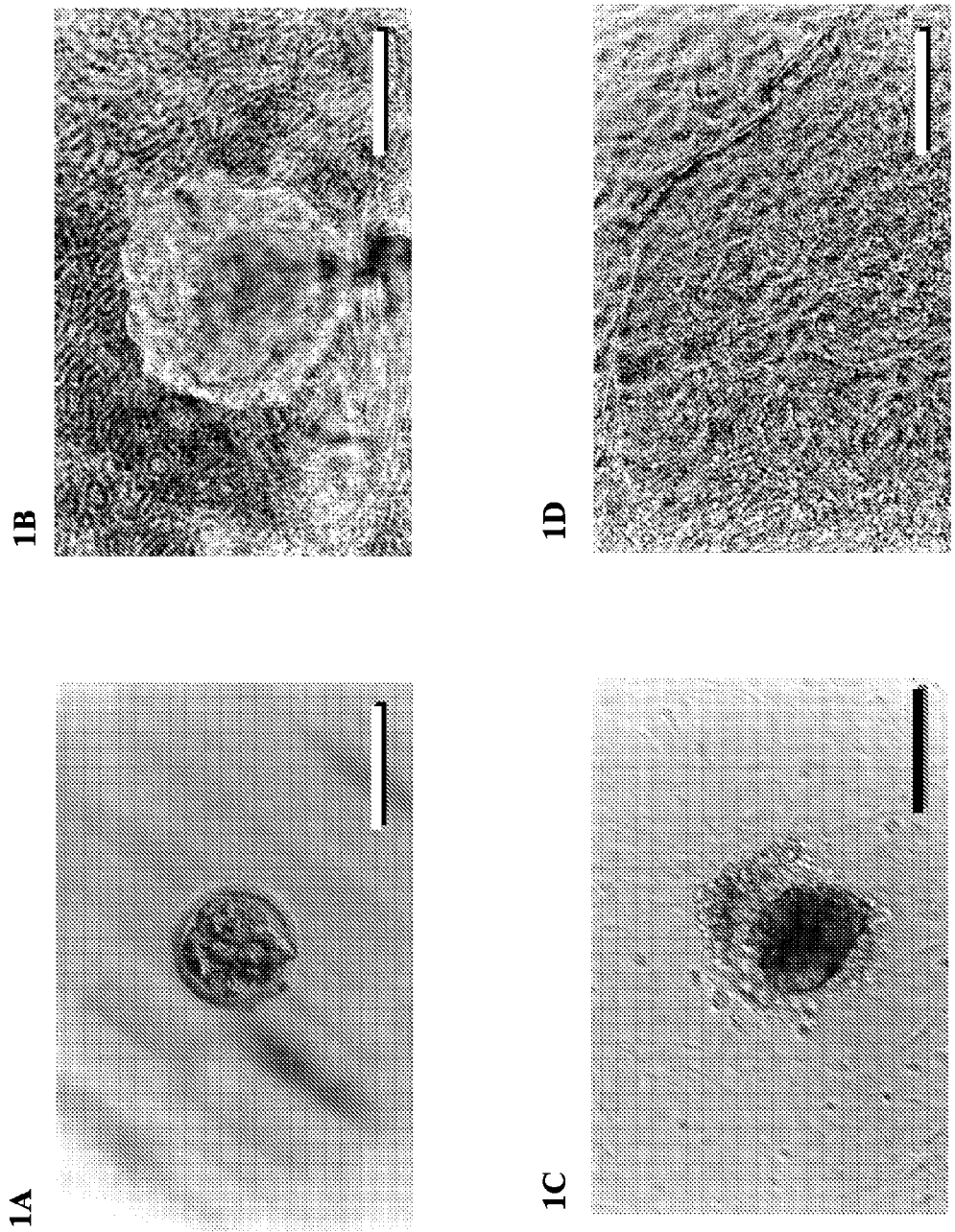
FIGs. 1A-D

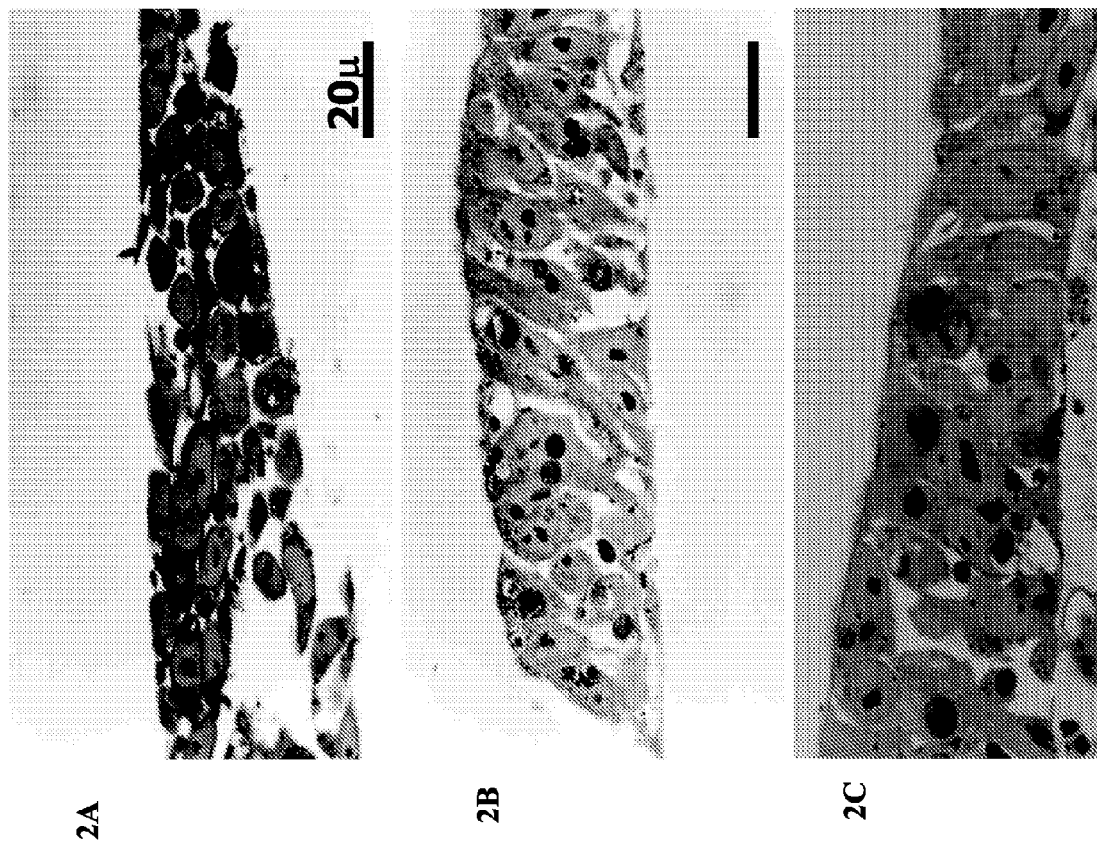

FIGs. 2D-E
2D
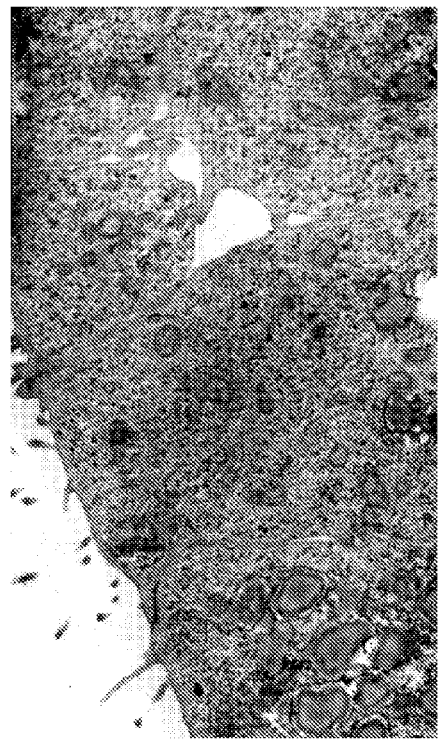
2E

FIGs. 3A-G
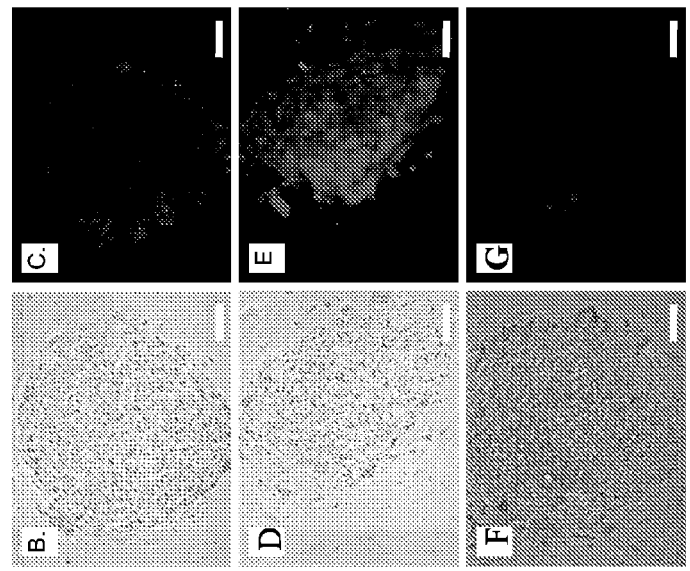
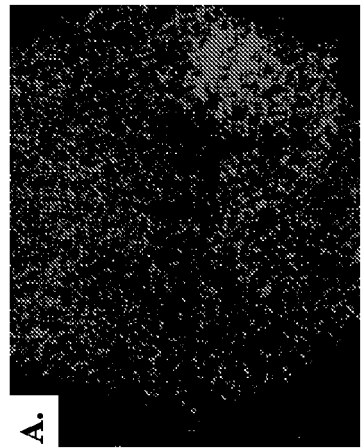

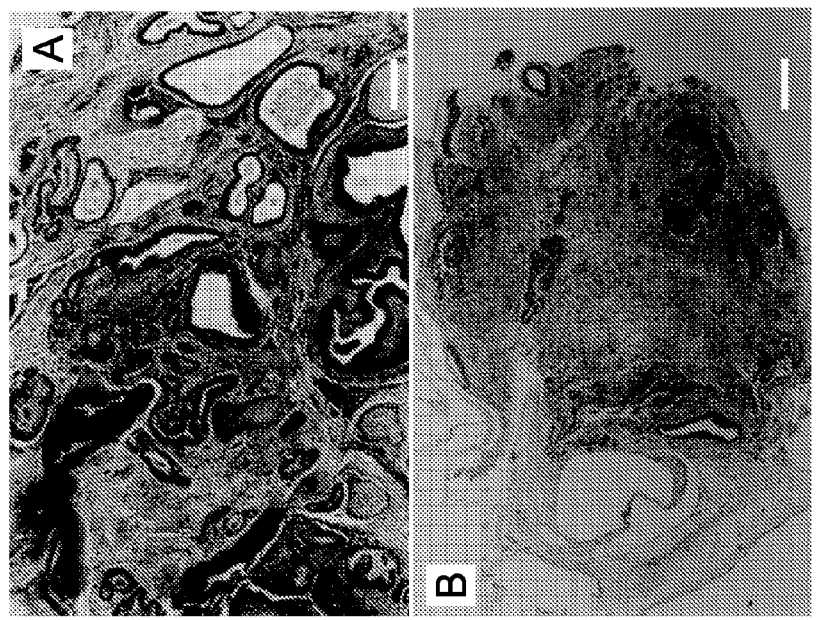
FIGs. 4A-B

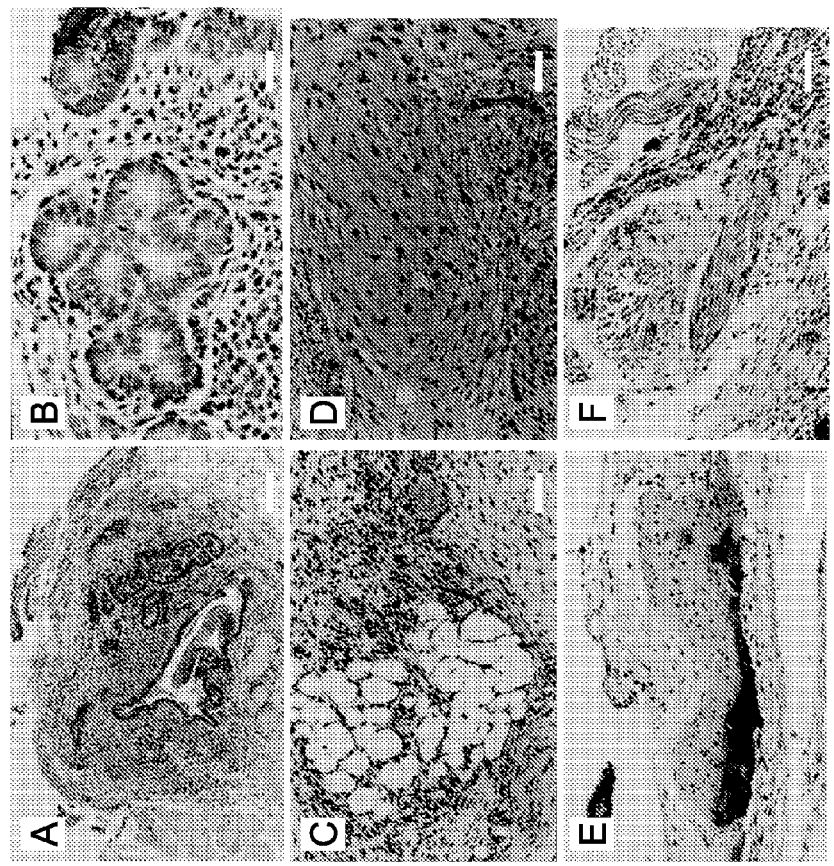
FIGs. 5A-F

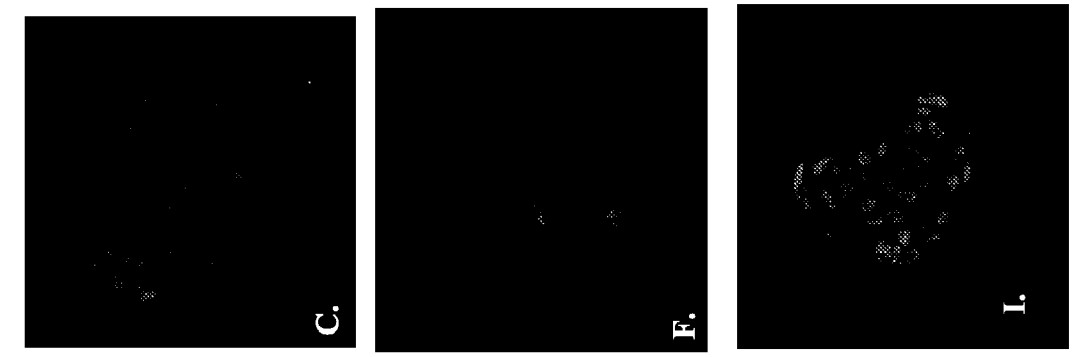
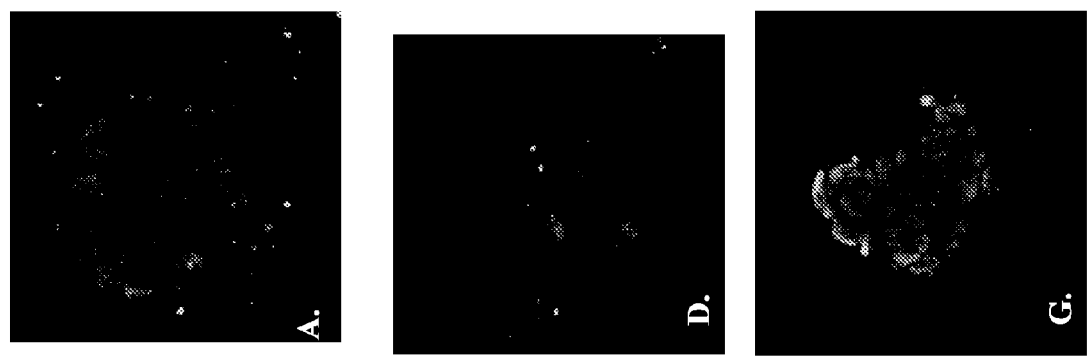
Figs. 9A-I.

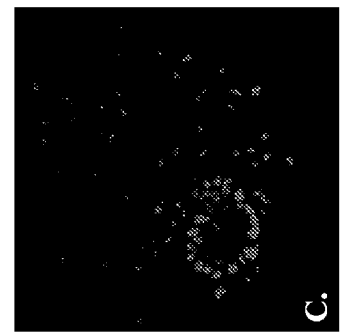
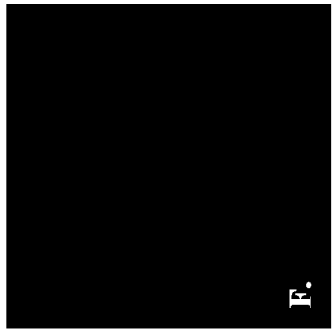
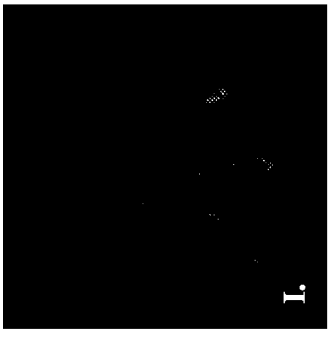
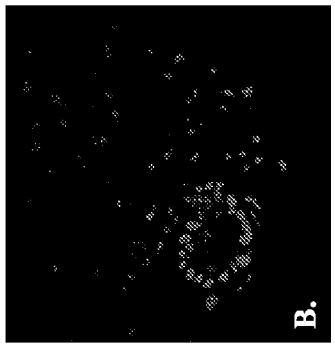
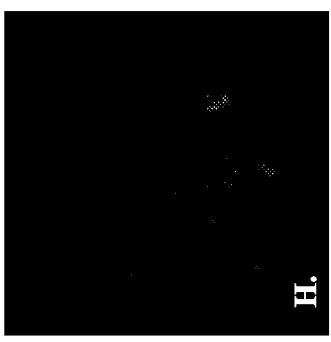
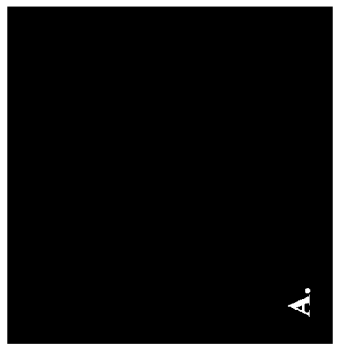
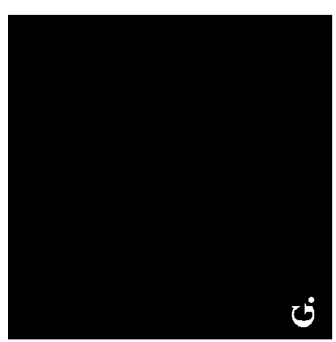
FIGs. 10A-I

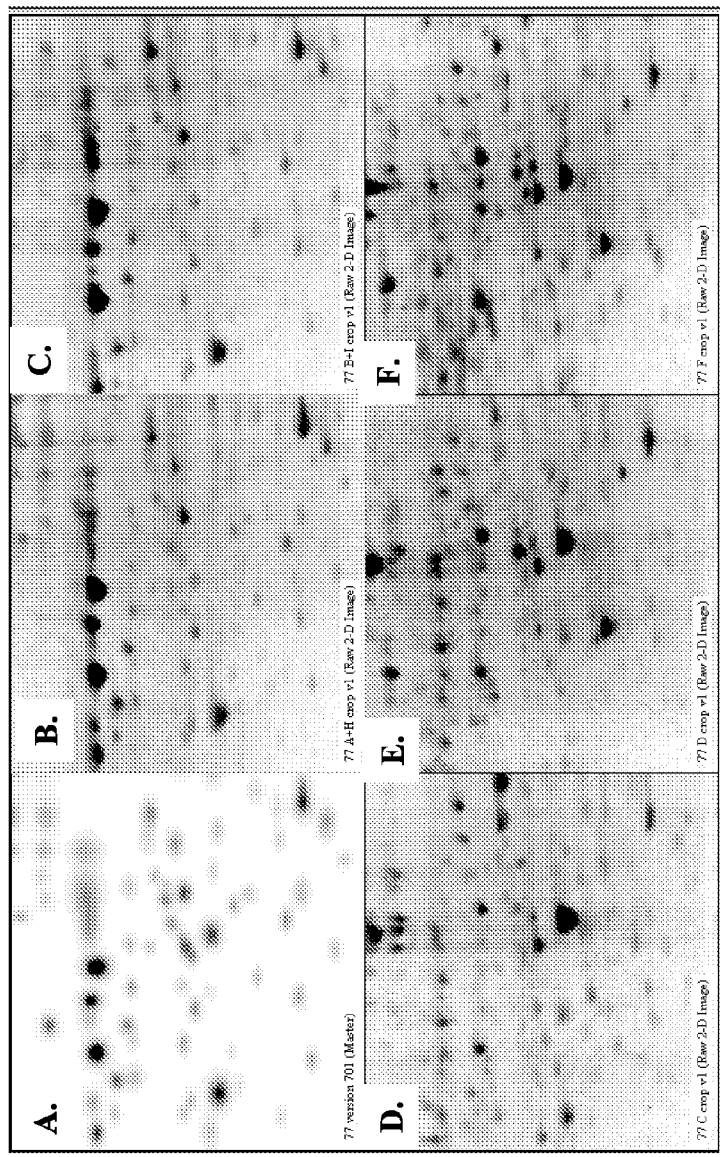
FIGs. 13A-F

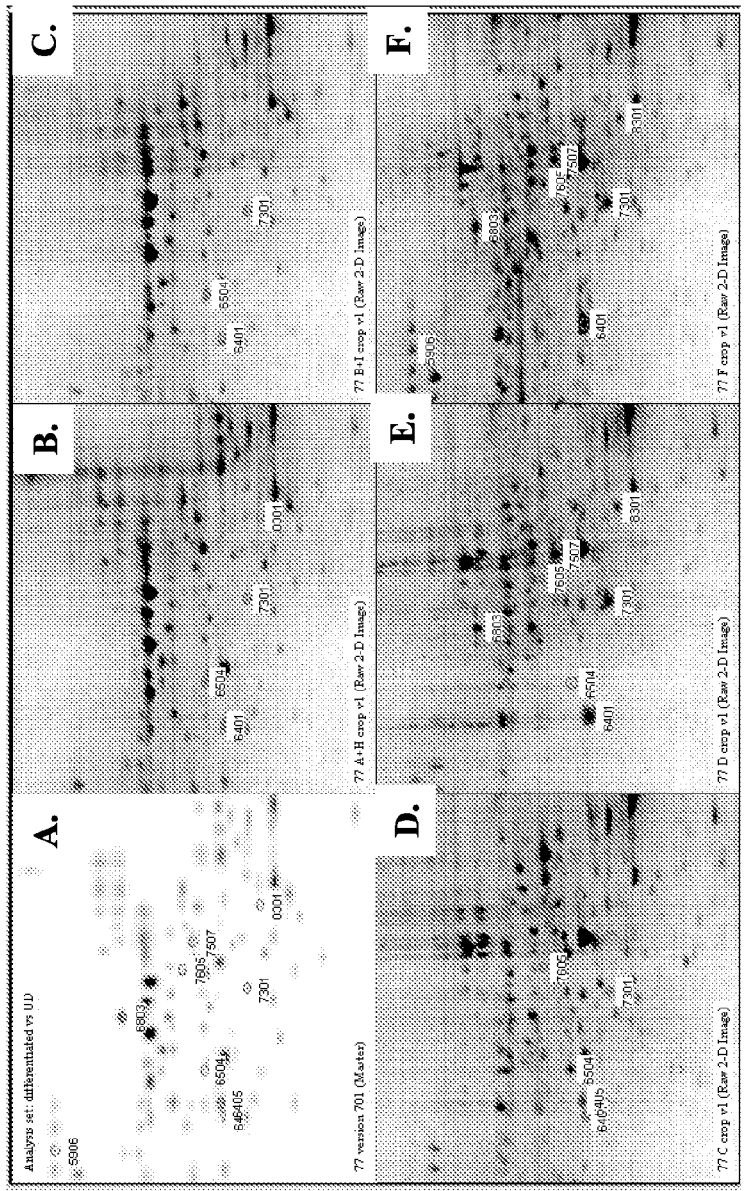
FIGs. 14A-F

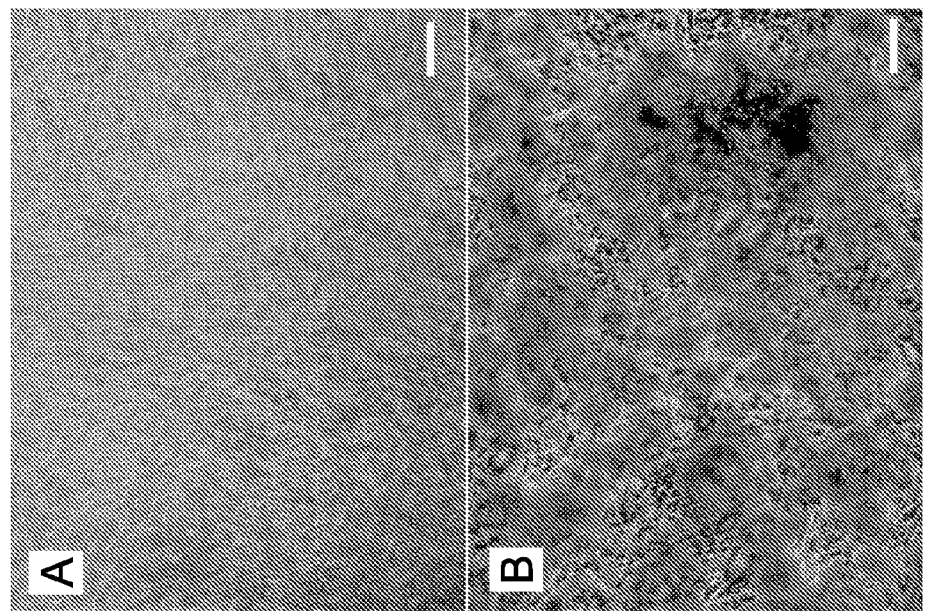
FIGs. 15A-B

ISOLATED PRIMATE EMBRYONIC CELLS DERIVED FROM EXTENDED BLASTOCYSTS

RELATED APPLICATIONS

This Application is a National Phase of PCT Patent Application No. PCT/IL2005/001074 having International Filing Date of Oct. 11, 2005, which claims the benefit of U.S. Provisional Patent Application No. 60/617,045 filed on Oct. 12, 2004. The contents of the above Applications are all incorporated herein by reference.

FIELD AND BACKGROUND OF THE INVENTION

The present invention relates to cells derived from delayed blastocysts and to cell lines generated therefrom.

Embryonic development starts soon after fertilization with blastomer cleavage, proliferation and differentiation. The blastomers within the developing mammalian embryo remain totipotent until the morula compaction stage. In the compacted embryo, the blastomers initiate polarization which results in two distinct cell-populations; the inner cell mass (ICM), which contributes to the embryo, and the outer trophectoderm layer, which develops into the extra embryonic layers. It is at this stage of embryogenesis—towards the end of the first week of development that embryonic stem (ES) cells are traditionally derived from the inner cell mass of the blastocyst.

At the time of implantation, the ICM is separated into a layer of primitive endoderm, which gives rise to the extra embryonic endoderm, and a layer of primitive ectoderm, which gives rise to the embryo proper and to some extra embryonic derivatives [Gardner J. Embryological Experiment and Morphology, 1982; 68: 175-198]. During the next major phase of development, termed gastrulation, the embryonic ectoderm differentiates into the three primary germ layers—endoderm (inside layer), mesoderm (middle layer), and ectoderm (outer layer). The cells become progressively restricted to a specific lineage, losing their pluripotency and thus are regarded as multi-potent progenitor cells. Therefore, pluripotent embryonic stem cells proliferate and replicate in the intact embryo only for a limited period of time.

Embryonic stem cells are characterized by their ability to propagate indefinitely in culture, as undifferentiated cells, while they can be induced to differentiate in vivo into teratomas when injected into SCID mice [Thomson, J. A., et al., (1998), Science, 282, 1145-1147; Reubinoff, B. E., et al., (2000), Nature Biotechnol., 18, 399-404]. They may also differentiate in vitro into embryoid bodies (EBs) that contain embryonic cells from the three germ layers (endoderm, mesoderm, and ectoderm). Moreover, this differentiation can be somewhat directed by the addition of growth factors into the culture media.

Human ES cells may also be genetically manipulated in culture [Eiges et al., (2001) Curr. Biol., 11, 514-518] and the transfected cells remain pluripotent and retain a normal karyotype [Shuldiner et al., (2003) Stem Cells 21, 257-265].

As a result of their unique features, it has been suggested that human ES cells hold the promise of changing the face of cell transplantation, by replacing or restoring tissue that has been damaged by disease or injury. Replacement of non-functional cells using ES cells technology can offer a lifelong treatment. Thus, diseases that might be treated by transplanting human ES-derived cells include Parkinson's disease, diabetes, traumatic spinal cord injury, Purkinje cell degeneration, Duchenne's muscular dystrophy, heart failure, and osteogenesis imperfecta.

Many other potential uses of human ES cells have been proposed that do not involve transplantation. For example, human ES cells could be used to study early events in human development. Human ES cells could also be used to test candidate therapeutic drugs or potential toxins by directing their differentiation into specific cell types. ES-derived cells may be more likely to mimic the in vivo response to the drug(s) being tested than animal and other in-vitro models and so offer safer, and potentially cheaper, models for drug screening.

Finally, human ES cells could be used to develop new methods for genetic engineering. Currently, the genetic complement of mouse ES cells in vitro can be modified easily by techniques such as homologous recombination. Using this method, genes to direct differentiation to a specific cell type or genes that express a desired protein product might be introduced into the ES cell line. Ultimately, if such techniques could be developed using human ES cells, it may be possible to devise better methods for gene therapy.

At present the only source for embryonic stem cells is the pre-implantation blastocyst embryo.

The pluripotency of human post-implantation embryonic cells between the time of implantation and the gastrulation process has as yet never been examined. Surani and Edwards teach in vitro culturing techniques of human embryos to day 9, demonstrating the presence of proliferating and healthy ICM [Edwards R. G., Surani M. A. H. (1978) Upsala Journal of Medical Sciences 22: 39-50].

However, they did not examine the pluripotency of stem cells at this post-implantation stage and did not isolate or culture them to allow their characterization.

Rathjen and colleagues teach a method for homogenous differentiation of mouse embryonic stem cells into early primitive ectoderm-like (EPL) using conditioned medium of Hep G2 cells [Rathjen et al. 1999, J. of Cells Science 112, 601-612] and demonstrate some similarities between them and the embryonic stem cells of the present invention. For example both cell types have a colony morphology of epithelial-like structures, a higher tendency to differentiate into mesodermal tissues and a reduced ability to either integrate into the embryonic germ layers after injection into mouse blastocysts [Lake et al. 2000, J. of Cells Science 113, 555-566] or form teratomas. However, in sharp contrast to the embryonic stem cells of the present invention, the EPLs unique features together with their ability to be cultured for limited passages in vitro are irreversible when the Hep G2 conditioned medium is removed [Rathjen et al. 1999 J. of Cells Science 112, 601-612; Lake et al. 2000, J. of Cells Science 113, 555-566]. The gene expression pattern of these cells is also different. The EPL cells, for example, express brachyury only as early EBs and not as undifferentiated cells like the embryonic stem cells of the present invention [Rathjen et al., 2000 J Cell Sci. 2000 113:555-66]. Together with the fact that the isolated EPLs are non-primate cells, the above mentioned differences indicate distinct cell populations.

The very broad range of potential applications for embryonic stem cells suggests that the identification of additional sources together with the novel stem cell lines derived therefrom, will be of critical importance for medical research in general and the advancement of stem cell research in particular.

SUMMARY OF THE INVENTION

According to one aspect of the present invention there is provided an isolated primate embryonic cell characterized by expression of brachyury and ability to differentiate to derivatives of each of an endoderm, mesoderm, and ectoderm tissue.

According to another aspect of the present invention there is provided a cell culture comprising the isolated primate embryonic cell characterized by expression of brachyury and ability to differentiate to derivatives of each of an endoderm, mesoderm, and ectoderm tissue.

According to yet another aspect of the present invention there is provided a method of generating a primate embryonic cell culture comprising providing a blastocyst of at least nine days post fertilization, isolating cells from the blastocyst; and culturing the isolated cells, thereby generating the primate embryonic cell culture.

According to still another aspect of the present invention there is provided a method of generating a primate embryonic cell line comprising providing a blastocyst of at least nine days post fertilization; isolating cells from the blastocyst; culturing the isolated cells; and cloning at least one of the isolated cells, thereby generating the primate embryonic cell line.

According to an additional aspect of the present invention there is provided a pharmaceutical composition comprising as an active ingredient a cell characterized by expression of brachyury and ability to differentiate to derivatives of each of an endoderm, mesoderm, and ectoderm tissue and a pharmaceutically acceptable carrier.

According to yet an additional aspect of the present invention there is provided a method of treating or preventing a disease in which cell transplantation is therapeutically beneficial comprising inducing cell differentiation in the isolated human embryonic cell characterized by expression of brachyury and ability to differentiate to derivatives of each of an endoderm, mesoderm, and ectoderm tissue and transplanting a therapeutically effective amount of the differentiated cells into a subject in need thereof, thereby preventing or treating a disease in which cell transplantation is therapeutically beneficial.

According to still an additional aspect of the present invention there is provided a method of generating a lineage specific cell comprising inducing a lineage-specific cell differentiation in the isolated primate embryonic cell characterized by expression of brachyury and ability to differentiate to derivatives of each of an endoderm, mesoderm, and ectoderm tissue, thereby generating the lineage specific cell.

According to further features in preferred embodiments of the invention described below, the isolated primate embryonic cell further expresses at least one cartilage marker According to still further features in the described preferred embodiments, the at least one cartilage marker is selected from the group consisting of COMP, aggrecan and collagen type II.

According to still further features in the described preferred embodiments, the cell culture further comprises feeder cells.

According to still further features in the described preferred embodiments, the cell culture, further comprises growth medium.

According to still further features in the described preferred embodiments, the providing the blastocyst is effected by ex-vivo culturing the blastocyst.

According to still further features in the described preferred embodiments, the ex-vivo culturing the blastocyst is effected on feeder cells.

According to still further features in the described preferred embodiments, the ex-vivo culturing the blastocyst is effected on a synthetic surface.

According to still further features in the described preferred embodiments, the culturing the isolated cells is effected on feeder cells.

According to still further features in the described preferred embodiments, the culturing the isolated cells is effected on a synthetic surface.

According to still further features in the described preferred embodiments, the isolated primate embryonic cell maintains a stable normal karotype for at least one year.

According to still further features in the described preferred embodiments, the isolated primate embryonic cell expresses SSEA4 and TRA-1-60 markers.

According to still further features in the described preferred embodiments, the isolated primate embryonic cell does not express SSEA1 marker.

According to still further features in the described preferred embodiments, the isolated primate embryonic cell expresses less TRA-1-81 marker than an embryonic stem cell of the same primate species not expressing brachyury using identical assay conditions.

According to still further features in the described preferred embodiments, the isolated primate embryonic cell is capable of colony organization of columnar epithelium with villi throughout the upper side of the colony.

According to still further features in the described preferred embodiments, the isolated primate embryonic cell has an OCT4 protein level lower than the OCT4 protein level in an embryonic stem cell of the same primate species not expressing brachycury using identical assay conditions.

According to still further features in the described preferred embodiments, the isolated primate embryonic cell expresses more mesodermal differentiating markers than an embryonic stem cell of an identical primate not expressing brachyury using identical assay conditions.

According to still further features in the described preferred embodiments, the isolated primate cell is genetically modified.

According to still further features in the described preferred embodiments, the feeder cells are mouse feeder cells or human feeder cells.

According to still further features in the described preferred embodiments, the mouse feeder cells are mitotically inactivated mouse embryonic fibroblasts or primary mouse embryonic fibroblasts.

According to still further features in the described preferred embodiments, the human feeder cells are selected from the group comprising embryonic fibroblast cells, adult fallopian epithelial cells and foreskin cells.

According to still further features in the described preferred embodiments, the isolated primate embryonic cell is in an undifferentiated proliferative state for at least 100 passages.

According to still further features in the described preferred embodiments, the isolated primate embryonic cell is immortalized.

According to still further features in the described preferred embodiments, the primate is a human.

According to still further features in the described preferred embodiments, the method of treating or preventing a disease in which cell transplantation is therapeutically beneficial further comprises genetically modifying the differentiated cell to express a therapeutic agent.

According to still further features in the described preferred embodiments, the inducing cell differentiation comprises genetically modifying a plurality of the cells.

The present invention successfully addresses the shortcomings of the presently known configurations by providing a Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

The file of this patent contains at least one drawing executed in color photograph. Copies of this patent with color photograph(s) will be provided by the Patent and Trademark Office upon request and payment of necessary fee.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-E are photographs of light microscopy images depicting the generation of extended blastocyst cell lines (EBCs). FIGS. 1A-D depict the generation of the J3 cell line. FIG. 1A depicts an early blastocyst prior to plating on mouse embryonic feeder cells (MEFs). Hoffman resolution bar=120 µM. FIG. 1B depicts the identical human embryo following plating for five days on MEFs. Hoffman resolution bar=120 µM. FIG. 1C depicts the identical human embryo following plating for nine days on MEFs. Hoffman resolution bar=120 µM. FIG. 1D depicts the resulting EBC cells. Hoffman resolution bar=20 µM. FIG. 1E depicts an extended blastocyst cell line (J6) following a second passage for ten days on MEFs. The yellow line represents the outline of a condense area containing the stem cells. Hoffman resolution bar=135 µM.

FIGS. 2A-E are photographs of light (FIGS. 2A-C; Hoffman resolution bar=20 µM; H&E staining) and electron (2D-E; Hoffman resolution bar=8 µM) microscopy images depicting the organization of EBC and ESC colonies. FIG. 2A depicts the organization of an ESC colony I6. FIG. 2B depicts the organization of the EBC colony J3. FIG. 2C depicts the organization of the EBC colony J6. FIG. 2D depicts the organization of the pre-implantation cell line H9 as observed with electron microscopy. FIG. 2E depicts the organization of the EBC cell line J3 as observed with electron microscopy.

FIGS. 3A-G are a series of photographs depicting the fluorescent immunostaining with stage specific markers of EBCs and ESCs. FIG. 3A depicts J3 colony staining with SSEA4. FIGS. 3B and 3C depict DM-1 (an hESC line derived from ICM) staining with SSEA4 under a light (FIG. 3B) and fluorescent (3C) microscope. FIGS. 3D and 3E depict DM-1 staining with TRA-1-6 under a light (FIG. 3D) and fluorescent (FIG. 3E) microscope. FIGS. 3F and 3G depict WS-1 (an HESC line derived from ICM) staining with TRA-1-81 under a light (FIG. 3F) and fluorescent (FIG. 3G) microscope. Phase contrast Bar=50 µM.

FIGS. 4A-B are photographs of teratoma sections stained with hematoxylin/eosin (H&E) as observed under a light microscope. Hoffman resolution bar=20 µM. The teratomas were generated following introduction of cells from I5 (FIG. 4A) and J2 (FIG. 4B) cell lines into four-week-old male SCID-beige mice.

FIGS. 5A-F are photographs of teratoma sections of EBC lines stained with H&E as observed under a light microscope demonstrating representative tissues of the three embryonic germ layers. The teratomas were generated following introduction of cells from J2 cell lines into four-week-old male SCID-beige mice. FIG. 5A depicts epithelium. Hoffman resolution bar=100 µM. FIG. 5B depicts secretory glands. Hoffman resolution bar=40 µM. FIG. 5C depicts fat tissue. Hoffman resolution bar=40 µM. FIG. 5D depicts mesenchymal tissue. Hoffman resolution bar=40 µM. FIG. 5E depicts bone tissue. Hoffman resolution bar=40 µM. FIG. 5F depicts myelinated nerve. Hoffman resolution bar=60 µM.

FIG. 8A is a dot graph comparing the gene expressions of two different hESC lines. FIG. 8B is a dot graph comparing the gene expressions of two different EBC cell lines. FIG. 8C is a dot graph comparing the average gene expression of hESC with EBC cell lines. FIG. 8D is a representative example of the chip.

FIGS. 9A-I are photographs of the J6 undifferentiated EBC cell line double stained with brachyury and Oct-4. FIGS. 9A, 9D and 9G depict brachyury staining alone. FIGS. 9C, 9F and 9I depict Oct-4 staining alone and FIGS. 9B, 9E and 9H depict the combined staining of both brachyury and Oct-4. Phase contrast bar=20 µM.

FIGS. 10A-I are photographs of the I3 hESC cell line double stained with brachyury and Oct-4. FIGS. 10A, 10D and 10G depict brachyury staining alone. FIGS. 10C, 10F and 10I depict Oct-4 staining alone and FIGS. 10B, 10E and 10H depict the combined staining of both brachyury and Oct-4. FIGS. 10A-C are of a differentiating colony of hESC lines; FIGS. 10D-F are of an undifferentiated colony of hESC line; FIGS. 10G-I are of an undifferentiated colony of hESC line. Phase contrast bar=20 µM.

FIG. 11A is a dendrogram based on the similarity between the four tested lines (I3, I6 J3 and J6). The following calculation settings were used: Columns included: J6 Signal, Z Scores, I3 Signal, Z Scores, I6 Signal, Z Scores, J3 Signal, Z Scores, Empty values replaced by: 0; Clustering method: Complete linkage (maximum); Similarity measure: Correlation; Ordering function: Average value. FIG. 11B is a heat map of the 238 probe sets which were significantly different in I cell lines and the J cell lines with a maximum p-value of 0.05.

Figure 12:
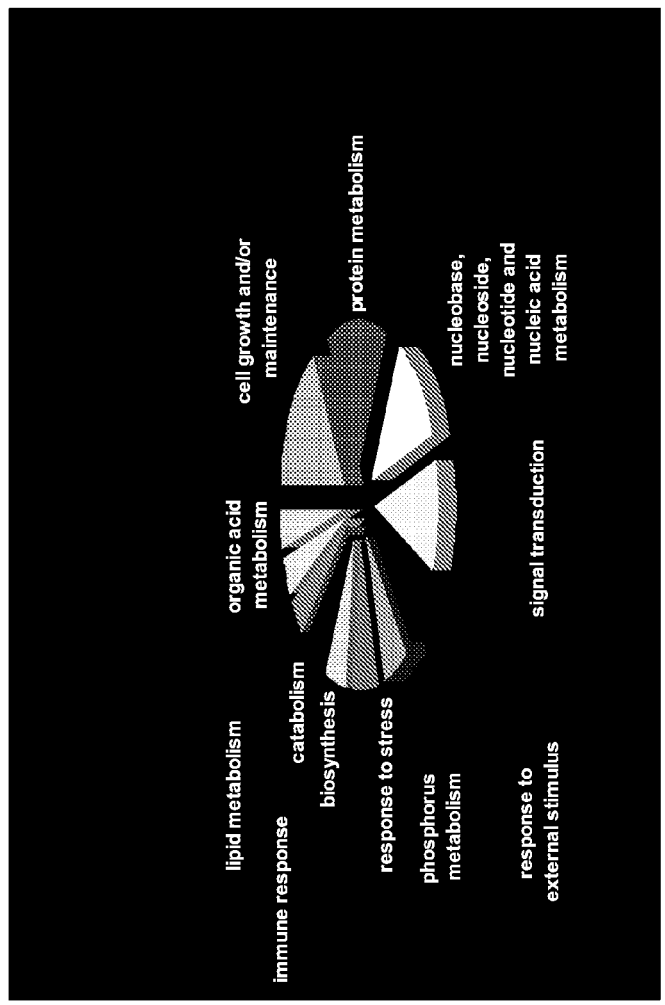

FIG. 12 is a pie chart illustrating the results obtained following Go-Chat analysis of the 238 probe sets which were significantly different in I cell lines and the J cell lines with a maximum p-value of 0.05.

FIGS. 13A-F are photographs of two-dimensional gel electrophoresis of an area within the gel that clearly differs between 5-day old EBs and undifferentiated hESCs. All treatments were performed on cells from the I4 cell line. FIG. 13A is a photograph of the Master gel (i.e. a gel on which MEF protein extract alone has been run) following two-dimensional gel electrophoresis. FIG. 13B is a photograph of two-dimensional gel electrophoresis of MEFs used to culture the hESCs. FIG. 13C is a duplicate of 13B. FIG. 13D is a photograph of two-dimensional gel electrophoresis of undifferentiated hESCs. FIG. 13E is a photograph of two-dimensional gel electrophoresis of hESCs that were cultured for 10 days as monolayers. FIG. 13F is a photograph of two-dimensional gel electrophoresis of 5-days old EBs.

FIGS. 14A-F are photographs of two-dimensional gel electrophoresis demonstrating an area within the gel that clearly differs between differentiated hESCs and undifferentiated hESCs. All treatments are performed on cells from the I4 cell line. FIG. 14A is a photograph of the Master gel following two-dimensional gel electrophoresis. FIG. 14B is a photograph of two-dimensional gel electrophoresis of MEFs used to culture the hESCs. FIG. 13C is a duplicate of 14B. FIG. 14D is a photograph of two-dimensional gel electrophoresis of undifferentiated hESCs. FIG. 14E is a photograph of two-dimensional gel electrophoresis of hESCs that were cultured for 10 days as monolayers. FIG. 14F is a photograph of two-dimensional gel electrophoresis of differentiated hESCs.

FIGS. 15A-B are photographs of Alizarin Red stained EB derived cells (EBDs). FIG. 15A depicts EBDs resulted from I4 (hESC) cells and FIG. 15B depicts EBDs from J6 cells (DBC) treated with the same medium supplemented with $TGF_{\beta 3}$. While the hESC demonstrated no positive staining the DBC cells demonstrated large area of clear red staining. FIG. 15A: Bar=15 μM and FIG. 15B: Bar=50 μM.

DESCRIPTION OF THE PREFERRED EMBODIMENTS

The present invention is of isolated primate embryonic stem cells and methods of generating stem cell cultures and cell lines therefrom. Specifically, the present invention relates to isolated embryonic stem cells which are characterized by expression of brachyury and their ability to differentiate to derivatives of endoderm, mesoderm, and ectoderm tissues.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Embryonic stem cells are characterized by their ability to propagate indefinitely in culture, as undifferentiated cells, while they can be induced to differentiate in vivo into teratomas when injected into SCID mice [Thomson, J. A., et al., (1998), Science, 282, 1145-1147; Reubinoff, B. E., et al., (2000), Nature Biotechnol., 18, 399-404]. They may also differentiate in vitro into embryoid bodies (EBs) that contain embryonic cells from the three germ layers (endoderm, mesoderm, and ectoderm) [Itskovitz-Eldor, J. et al., Mol. Med., 6, 88-95]. Moreover, this differentiation can be somewhat directed by the addition of growth factors into the culture media [Schuldiner, M et al., (2000) P.N.A.S. USA, 97, 11307-11312]. For example, ES cells can be induced to differentiate in vitro into cardiomyocytes [Paquin et al., Proc. Nat. Acad. Sci. (2002) 99:9550-9555], hematopoietic cells [Weiss et al., Hematol. Oncol. Clin. N. Amer. (1997) 11(6):1185-98; U.S. Pat. No. 6,280,718], insulin-secreting beta cells [Assady et al., Diabetes (2001) 50(8):1691-1697], and neural progenitors capable of differentiating into astrocytes, oligodendrocytes, and mature neurons [Reubinoff et al., Nature Biotechnology (2001) 19:1134-1140; U.S. Pat. No. 5,851,832].

Human ES cells may also be genetically manipulated in culture [Eiges et al., (2001) Curr. Biol., 11, 514-518] and the transfected cells remain pluripotent (i.e., capable through its progeny of giving rise in vivo to all the cell types which comprise the adult animal including the germ cells) and retain a normal karyotype [Shuldiner et al., (2003) Stem Cells 21, 257-265].

As a result of their unique features, it has been suggested that human ES cells hold the promise of changing the face of cell transplantation, by replacing or restoring tissue that has been damaged by disease or injury. Replacement of non-functional cells using ES cells technology can offer a lifelong treatment. Thus, diseases that might be treated by transplanting human ES-derived cells include Parkinson's disease, diabetes, traumatic spinal cord injury, Purkinje cell degeneration, Duchenne's muscular dystrophy, heart failure, and osteogenesis imperfecta.

ESCs have been successfully isolated from primates (Thomson et al., 1998 Science, 282, 1145-1147; Amit et al., 2000 Dev. Biol. 227: 271-8), mice (Mills and Bradley, 2001, Trends Genet. 17: 331-9) and other species where they are derived from the inner cell mass (ICM) of the mammalian blastocyst prior to the implantation stage.

Whilst reducing the present invention to practice, the present inventors have uncovered that human embryonic stem cells may be derived from a post-implantation stage blastocyst. Moreover these stem cells display different characteristics to the traditional embryonic stem cells derived form pre-implantation stage blastocysts while are still capable of differentiating to all the cell types which comprise the adult animal (Example 3, FIGS. 4A-B and 5A-F) and therefore represent a novel class of embryonic stem cell.

Thus, as described in the Examples section which follows embryonic stem cells derived from post-implantation/pre-gastrulation stage blastocysts [referred to herein as extended blastocyst cells (EBCs)] display a different colony morphology (FIGS. 2A-E) and express different levels of both cell surface markers and differentiation markers to ESCs derived from pre-implantation stage blastocysts. Specifically, EBCs express many early differentiation markers, mostly mesodermal, as demonstrated by RT-PCR (Table 3, Example 3 and FIG. 7), histochemistry (FIGS. 3A-X, 9A-I and 10A-I), two-dimensional gel electrophoresis (FIGS. 13A-F and 14A-F) and chip DNA analysis (FIGS. 8A-D, 11A-B and 12).

It will be appreciated that although ex vivo culturing of human embryos until day 9 has been previously reported, the prior art does not teach of stem cell isolation or culturing. Moreover, the pluripotency of these stem cells at this post-implantation stage was not examined [Edwards R. G., Surani M. A. H. (1978) Upsala Journal of Medical Sciences 22: 39-50].

Thus, according to one aspect of the present invention there is provided an isolated primate embryonic cell characterized by expression of brachyury and ability to differentiate to derivatives of each of an endoderm, mesoderm, and ectoderm tissue.

As used herein the phrase "primate embryonic cell" refers to a cell from embryonic primate origin. Typically the embryonic cell of this aspect of the present invention has a high nuclear/cytoplasmic ratio and prominent nucleolus.

As used herein the term "primate" refers to both higher and lower primates. Preferably the primate is a human.

According to this aspect of the present invention, the term "isolated" refers to an embryonic cell or a plurality of embryonic cells that have been removed from their naturally-occurring in-vivo environment (i.e. post-implantation/pre-gastrulation stage blastocyst). Preferably the isolated embryonic cell of this aspect of the present invention (i.e., expressing Brachyury and being capable of differentiating to derivatives of each of an endoderm, mesoderm, and ectoderm tissue) is substantially free from other substances (e.g., other cells, proteins, nucleic acids, etc.) that are present in its in-vivo environment. Methods for removing embryonic cells from a post-implantation/pre-gastrulation stage blastocyst are described hereinbelow and in the Examples section which follows.

As used herein, the term "brachyury" refers to the human T-box transcription factor, of Swiss Prot No. O15178 and homologues and orthologues thereof, such as encoded by the polynucleotide sequences listed in Table 1 below.

TABLE 1

| Species | GenBank Accession Number |
|---|---|
| Chimpanzee | 472186 |
| Chimpanzee | XM_527563.1 |
| Chimpanzee | XP_527563.1 |

As used herein, the phrase "expression of brachyury" refers to mRNA/protein expression of brachyury. Preferably, the endogenous expression of Brachyury in the isolated cells of the present invention is at least two times higher, preferably at least five times higher and more preferably at least ten times higher than the endogenous expression of Brachyury protein in embryonic stem cells derived from pre-implantation blastocysts. Increased expression of Brachyury protein may be confirmed using standard techniques known in the art further described hereinbelow.

As used herein, the phrase "derivatives of each of an endoderm, mesoderm and ectoderm tissue" encompasses fully or partially differentiated cells. This characteristic of the cells of the present invention resembles the ability of embryonic stem cells to derivatives of each of an endoderm, mesoderm and ectoderm tissue. Examples of endoderm derivatives include, but are not limited to, hepatocytes and pancreatic cells. Examples of mesoderm derivatives, include but are not limited to, osseous, cartilaginous, elastic, fibrous connective tissues, myocytes, myocardial cells, bone marrow cells, vascular cells (namely endothelial and smooth muscle cells), and hematopoietic cells. Examples of ectoderm derivatives include but are not limited to neural, retina and epidermal cells.

The isolated primate embryonic cells of the present invention may be obtained from a blastocyst of at least nine days post fertilization at a stage prior to gastrulation. Blastocysts less than nine days old may be obtained from in vivo preimplantation embryos, in vitro fertilized (IVF) embryos or from single cell embryos expanded to the blastocyst stage. Prior to culturing the blastocyst, the zona pellucida is digested (for example by Tyrode's acidic solution (Sigma Aldrich, St Louis, Mo., USA)) so as to expose the inner cell mass. The blastocysts are then cultured as whole embryos for at least nine and no more than fourteen days post fertilization (i.e. prior to the gastrulation event) in vitro using standard embryonic stem cell culturing methods.

Blasocyst culturing may be effected using currently practiced ES culturing methods. These are mainly based on the use of feeder cell layers which secrete factors needed for stem cell proliferation, while at the same time, inhibit their differentiation. Feeder cell-free systems have also been used in ES cell culturing, such systems utilize matrices supplemented with serum, cytokines and growth factors as a replacement for the feeder cell layer. The following summarizes culturing techniques which may be used in each of the steps of generating the embryonic cells of the present invention (also referred to as embryonic stem cells of the present invention). Currently preferred configuration of blastocyst culturing is described in Example 1 of the Examples section which follows.

Feeder-layer Based Cultures

Mouse feeder layers—The most common method for culturing ES cells is based on mouse embryonic fibroblasts (MEF) as a feeder cell layer supplemented with tissue culture medium containing serum or leukemia inhibitor factor (LIF) which supports the proliferation and the pluripotency of the ES cells [Thomson J A, Itskovitz-Eldor J, Shapiro S S, Waknitz M A, Swiergiel J J, Marshall V S, Jones J M. (1998). Embryonic stem cell lines derived from human blastocysts. Science 282: 1145-7; Reubinoff B E, Pera M F, Fong C, Trounson A, Bongso A. (2000). Embryonic stem cell lines from human blastocysts: somatic differentiation in vitro. Nat. Biotechnol. 18: 399-404]. MEF cells are derived from day 12-13 mouse embryos in medium supplemented with fetal bovine serum. Under these conditions mouse ES cells can be maintained in culture as pluripotent stem cells, preserving their phenotypical and functional characteristics. However, unlike mouse ES cells, the presence of exogenously added LIF does not prevent differentiation of human ES cells [Thomson J, Itskovitz-Eldor J, Shapiro S S, Waknitz M A, Swiergiel J J, Marshall V S, Jones J M. (1998). Embryonic stem cell lines derived from human blastocysts. Science 282: 1145-7; Reubinoff B E, Pera M F, Fong C, Trounson A, Bongso A. (2000). Embryonic stem cell lines from human blastocysts: somatic differentiation in vitro. Nat. Biotechnol. 18: 399-404]. Furthermore, the use of feeder cells substantially increases the cost of production, and makes scale-up of human ES cell culture impractical. Additionally, the feeder cells are metabolically inactivated to keep them from outgrowing the stem cells; hence it is necessary to have fresh feeder cells for each splitting of human ES culture. Since at present, the separation of feeder cell components from embryonic cells prepared in bulk culture cannot be efficiently achieved, feeder cell layer-prepared ES cultures are not suitable for human therapy.

ES cells can also be cultured on MEF under serum-free conditions using serum replacement supplemented with basic fibroblast growth factor (bFGF) [Amit M, Carpenter M K, Inokuma M S, Chiu C P, Harris C P, Waknitz M A, Itskovitz-Eldor J, Thomson J A. (2000). Clonally derived human embryonic stem cell lines maintain pluripotency and proliferative potential for prolonged periods of culture. Dev. Biol. 227: 271-8]. Under these conditions the cloning efficiency of ES cells is 4 times higher than under fetal bovine serum. In addition, following 6 months of culturing under serum replacement the ES cells still maintain their pluripotency as indicated by their ability to form teratomas which contain all three embryonic germ layers. Although this system uses a better-defined culture conditions, the presence of mouse cells in the culture exposes the human culture to pathogens which restricts their use in cell-based therapy.

Human embryonic fibroblasts or adult fallopian epithelial cells as feeder cell layers—Human ES cells can be grown and maintained using human embryonic fibroblasts or adult fallopian epithelial cells. When grown on these human feeder cells the human ES cells exhibit normal karyotypes, present alkaline phosphatase activity, express Oct-4 and other embryonic cell surface markers including SSEA-3, SSEA-4, TRA-1-60, and GCTM-2, form teratomas in vivo, and retain all key morphological characteristics [Richards M, Fong C Y, Chan W K, Wong P C, Bongso A. (2002). Human feeders support prolonged undifferentiated growth of human inner cell masses and embryonic stem cells. Nat. Biotechnol. 20: 933-6]. However, the major disadvantage of using human embryonic fibroblasts or adult fallopian tube epithelial cells as feeder cells is that both of these cell lines have a limited passage capacity of only 8-10 times, thereby limiting the ability of a prolonged ES growth period. For a prolonged culturing period, the ES cells must be grown on human feeder cells originated from several subjects which results in an increased variability in culture conditions.

Foreskin feeder layers—Human ES cells can be cultured on human foreskin feeder layer as disclosed in U.S. patent application Ser. No. 10/368,045. Foreskin derived feeder cell layers consist of a complete animal-free environment suitable for culturing human ES cells. In addition, foreskin cells can be maintained in culture for as long as 42 passages since their derivation, providing the ES cells with a relatively constant environment. Under these conditions the human ES cells were found to be functionally indistinct from cells grown with alternate protocols (e.g., MEF). Following differentiation, ES cells expressed genes associated with all three embryonal germ layers, in vitro, and formed teratomas in vivo, consisting of tissue arising from all three germ layers. In addition, unlike human fallopian epithelial cells or human embryonic fibroblasts, human ES cells cultured on foreskin feeder layers were maintained in culture in a pluripotent and undifferentiated state for at least 87 passages. However, although foreskin cells can be maintained in culture for long periods (i.e., 42 passages), the foreskin culture system is not well-defined due to differences between separate batches. In addition, human feeder layer-based culture systems would still require the simultaneous growth of both feeder layers and hES cells. Therefore, feeder-free culturing systems have been developed.

Feeder-Free Cultures

Stem cells can be grown on a solid surface such as an extracellular matrix (e.g., Matrigel® or laminin) in the presence of a culture medium. Unlike feeder-based cultures which require the simultaneous growth of feeder cells and stem cells and which may result in mixed cell populations, stem cells grown on feeder-free systems are easily separated from the surface. The culture medium used for growing the stem cells contains factors that effectively inhibit differentiation and promote their growth such as MEF-conditioned medium and bFGF. However, commonly used feeder-free culturing systems utilize an animal-based matrix (e.g., Matrigel®) supplemented with mouse or bovine serum, or with MEF conditioned medium [Xu C, et al. (2001). Feeder-free growth of undifferentiated human embryonic stem cells. Nat Biotechnol. 19: 971-4] which present the risk of animal pathogen cross-transfer to the human ES cells, thus compromising future clinical applications.

The embryonic stem cells of the present invention can be isolated by virtue of their morphology (e.g. small cell with large nucleus) and/or by any other stem cell distinguishing feature. Isolation may be achieved by chemical or mechanical means or both. Preferably mechanical isolation and removal by a micropipette is used. Mechanical isolation may be combined with a chemical or enzymatic treatment to aid with dissociation of the cells, such as $Ca^{2+}/Mg^{2+}$ free PBS medium or dispase.

The isolated embryonic stem cells of this invention may be cultured in any way which ensures their non-differentiated state as described hereinabove. An exemplary culturing medium comprises 85% ko-DMEM and supplemented with 15% ko-serum replacement, 1 mM L-glutamine, 0.1 mM β-mercaptoethanol, 1% non-essential amino acid stock and 4 ng/ml basic fibroblast growth factor (bFGF) (all products from Gibco Invitrogen corporation products, San Diego, Calif., USA).

Methods of qualifying the embryonic stem cells of the present invention are well known in the art. For example, differentiation state may be determined by injecting cells into a 8-12 week old SCID mice (FIGS. 5A-F) as described by Evans et al., [Evans M J and Kaufman M (1983) Cancer Surv. 2: 185-208], which upon injection form teratomas. Teratomas are typically fixed using 4% paraformaldehyde and histologically examined for the three germ layers. Alternatively, this can be confirmed by determining their ability to form embryonal bodies as described in Example 3 of the Examples section which follows.

The embryonic stem cells of the present invention can also be qualified by the expression of cell markers. Typically, expression of cell markers can be detected using a variety of cell biology, molecular biology and biochemical techniques which are well known in the art. For example flow cytometry may be used to detect membrane-bound markers, immunohistochemistry may be used to detect intracellular markers, and enzyme-linked immunoassays may be used to detect markers secreted into the medium. The expression of protein markers can also be detected at the mRNA level by reverse transcriptase-PCR (using marker-specific primers), Northern blots and oligonucleotide microarrays.

Thus, the embryonic stem cells of the present invention may be qualified by the expression of stage-specific embryonic antigens (SSEA). Antibodies for SSEA markers are available from the Developmental Studies Hybridoma Bank (Bethesda Md.). Other markers which are typically used for the qualification of embryonic stem cells are Tra-1-60 and Tra-1-81 (antibodies available from Chemicon International, Temecula, Canada) and Octamer binding transcription factor 4 (OCT-4) (Santa Cruz). OCT-4 (GenBank Accession No. NM_00270) is a member of the POU family of transcription factors. OCT-4 transcription is activated between the 4 and 80 cell stage in the developing embryo, and it is highly expressed in the expanding blastocyst and then in the pluripotent cells of the egg cylinder. Transcription is down-regulated as the primitive ectoderm differentiates to form mesoderm, and by 8.5 days post coitum is restricted to migrating primordial germ cells. Similar to embryonic stem cells not expressing brachyury, the embryonic stem cells of the present invention express SSEA4 and TRA-1-60 markers. However, in contrast to embryonic stem cells not expressing brachyury, the embryonic stem cells of the present invention do not express SSEA1 marker. In addition, the embryonic stem cells of the present invention express less TRA-1-81 and OCT-4 marker than embryonic stem cells not expressing brachyury using identical assay conditions.

The isolated primate embryonic stem cell of the present invention typically expresses more mesodermal differentiating markers than an embryonic stem cell of an identical primate not expressing brachyury. Typically, the isolated primate embryonic stem cells of the present invention express cartilage markers. Examples of cartilage markers which are expressed by the cells of the present invention include but are not limited to COMP (GenBank Accession No. L32137), aggrecan (GenBank Accession No. XI 7406) and collagen type II (GenBank Accession No. X06268).

Examples of other mesodermal differentiating markers that are expressed at a higher level in the embryonic stem cells of the present invention include, but are not limited to cartilage link protein (GenBank Accession No. U43328), cardiac actin (GenBank Accession No. NM_005159), BMP4 (GenBank Accession No. D30751) and BMP2 (GenBank Accession No. NM_001200).

Another method of qualification of embryonic stem cells is based on genetic analysis. Karotyping is one type of morphological analysis routinely performed for the qualification of embryonic stem cells. It is important in order to verify cytological euploidity, wherein all chromosomes are present and not detectably altered during culturing. Cultured stem cells can be karyotyped using a standard Giemsa staining and compared to published karyotypes of the corresponding species.

As is illustrated in Example 2 of the Examples section below, embryonic stem cells of the present invention retain a normal karyotype following at least twenty passages.

Microscopy is a type of morphological analysis routinely performed for the qualification of embryonic stem cells.

As demonstrated in Example 2 (FIGS. 2A-E) the isolated primate embryonic stem cells of the present invention are capable of a colony organization of columnar epithelium with villi throughout the upper side of the colony. Typically the colonies of embryonic stem cells not expressing brachyury are organized as stratified epithelium, with no villi facing the upper side (FIG. 2A). Furthermore, electron microscopy indicated that zonula occludente junctions, typical for columnar epithelium, could be detected between the embryonic stem cells of the present invention and not between the upper rows of embryonic stem cells not expressing brachyury (FIGS. 2D-E).

Preferably, the embryonic stem cells of the present invention remain in an undifferentiated proliferative state for at least 20, 30, 40, 50, 60, 70, 80, 90, preferably at least one hundred passages.

Stem cells generated according to the teachings of the present invention may be cultured on feeder cells or in a xenofree environment such as in the presence of synthetic extracellular matrix components (e.g., Matrigel™) as described above.

An isolated embryonic stem cell may be cloned from the culture described hereinabove in order to generate an embryonic stem cell line. Methods of cloning are well known in the art.

Cell lines of the present invention can be produced by immortalizing the cloned cells by methods known in the art, including, for example, expressing a telomerase gene in the cells (Wei, W. et al., 2003. Abolition of Cyclin-Dependent Kinase Inhibitor p16Ink4a and p21Cip1/Waf1 Functions Permits Ras-Induced Anchorage-Independent Growth in Telomerase-Immortalized Human Fibroblasts. Mol Cell Biol. 23: 2859-2870) or co-culturing the cells with NIH 3T3 hph-HOX11 retroviral producer cells (Hawley, R. G. et al., 1994. The HOX11 homeobox-containing gene of human leukemia immortalizes murine hematopoietic precursors. Oncogene 9: 1-12).

The embryonic stem cells may be further genetically modified at any stage of isolation. For example, they may be genetically modified through introduction of vectors expressing a selectable marker under the control of a stem cell specific promoter such as Oct-4. Some differentiated progeny of embryonic stem cells may produce products which are inhibitory to stem cell renewal or survival. Therefore selection against such differentiated cells, facilitated by the introduction of a construct such as that described above, may promote stem cell growth and prevent differentiation. The stem cells may be genetically modified at any stage with markers so that the markers are carried through to any stage of cultivation. The markers may be used to purify the differentiated or undifferentiated stem cell population at any stage of cultivation.

Alternatively, the embryonic stem cells of the present invention may be genetically modified to express a therapeutic agent or to direct differentiation into a specific cell lineage.

Various methods can be used to introduce an exogenous gene (e.g. the telomerase gene) in primate embryonic stem cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

The embryonic stem cells derived according to the teachings of the present invention can be used for several commercial and research applications.

Cultured embryonic stem cells of the present invention can be differentiated into restricted developmental lineage cells, or terminally differentiated cells.

Differentiation of stem cells can be initiated by allowing overgrowth of undifferentiated human ES cells in suspension culture forming embryoid bodies or by plating ES cells under conditions that promote differentiation in a particular manner. Such conditions may include withdrawing or adding nutrients, growth factors or cytokines to the medium, changing the oxygen pressure, or altering the substrate on the culture surface. For example, embryonic stem cells can be induced to differentiate in vitro into cardiomyocytes [Paquin et al., Proc. Nat. Acad. Sci. (2002) 99:9550-9555]. Several factors alone or in combination have been shown to enrich cardiac differentiation such as hepatocyte growth factor (HGF), epidermal growth factor (EGF), basic fibroblast growth factor (bFGF), transforming growth factor β1(TGF β1), platelet derived growth factor (PDGF), sphingosine-1-phosphate, retinoic acid, 5-azacytidine and vitamin C. Embryonic stem cells have also been induced to differentiate into neural or glial lineages [Reubinoff et al., Nature Biotechnology (2001) 19:1134-1140; U.S. Pat. No. 5,851,832]. For their generation, the medium typically includes any of the following factors or medium constituents in an effective combination: Brain derived neurotrophic factor (BDNF), neutrotrophin-3 (NT-3), NT-4, epidermal growth factor (EGF), ciliary neurotrophic factor (CNTF), nerve growth factor (NGF), retinoic acid (RA), sonic hedgehog, FGF-8, ascorbic acid, forskolin, fetal bovine serum (FBS), and bone morphogenic proteins (BMPs). Embryonic stem cells have also been induced to differentiate into hematopoietic cells [Weiss et al., Hematol. Oncol. Clin. N. Amer. (1997) 11(6):1185-98; U.S. Pat. No. 6,280,718] and insulin-secreting beta cells [Assady et al., Diabetes (2001) 50(8):1691-1697].

Differentiation of stem cells can also be directed by genetic modification. Several transcription factors have been demonstrated to regulate differentiation of ES cells to specific cell types [Levinson-Dushnik M., Benvenisty N., Cell Biol. 17: 3817-3822, 1997]. Ectopic over-expression of such factors stimulates ES cells to differentiate selectively into certain cell types. For example over-expression of the transcription factor GATA-4 was shown to induce cardiomyocyte differentiation [Grepin C., et al., Development 124: 2387-2395, 1997; Fujikura J., et al., Genes Dev. 16: 784-789, 2002; Kanda S., et al., Hepatol. Res. 26:225-231, 2003]. Techniques for the genetic modification of the present invention are described herein above.

Alternatively, the embryonic stem cells of the present invention may be seeded over a porous scaffold (e.g. an alignate scaffold) as described in U.S. Pat. Appl. No. 60/604,002 to allow the formation of embryoid bodies (EBs) thereby allowing partial differentiation. The three dimensional scaffolds may be coated with components of extracellular matrix such as fibronectin, laminin, collagen and/or supplemented with cytokines, growth factors and chemokines. Cell seeding is effected in a manner which enables even distribution of the cells on/within the scaffold. One approach which can be utilized to achieve even distribution is seeding under a centrifugal force (Dar et al., 2002, Biotechnol Bioeng 80:305-312). Cells are preferably seeded at a concentration which ensures entrapment within the scaffold and maximal formation of EBs preferably about $5 \times 10^7$ cells per cm$^3$ scaffold. The embryoid bodies may be further differentiated along specific cell lineages as described hereinabove.

Since the cells of the present invention may be differentiated in a lineage specific fashion, they may be used for human cell-based therapy and tissue regeneration.

Thus, according to another aspect of the present invention there is provided a method of treating a disease in which cell transplantation is therapeutically beneficial.

The method according to this aspect of the present invention is effected by inducing cell differentiation in the isolated human embryonic stem cell of the present invention and transplanting a therapeutically effective amount of the differentiated cells into a subject in need thereof, thereby preventing or treating a disease in which cell transplantation is therapeutically beneficial.

As used herein "a disease in which cell transplantation is therapeutically beneficial" refers a disease, conditions or disorder such as a neurological disorder (e.g. Parkinson's disease), a muscular disorder (e.g. muscular dystrophy), a cardiovascular disorder (e.g. heart failure), an hematological disorder (e.g. leukemia, lymphoma, thalassemia and sickle cell anemia), a metabolic disorder (e.g. Type I diabetes), a skin disorder (e.g. psoriasis), a liver disorder (e.g. acute liver failure) that may be treated by cell transplantation.

The phrase "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

As used herein, "transplanting" refers to a means for providing the differentiated embryonic stem cells of the present invention, using any suitable route, e.g., oral, sublingual intravenous, subcutaneous, transcutaneous, intramuscular, intracutaneous, intrathecal, intra peritoneal, intra spleenic, intra hepatic, intra pancreatic, intra cardiac, epidural, intraocular, intracranial, inhalation, rectal, vaginal, and the like. Cells may be transplanted as are or attached to a scaffold (matrix). Differentiation of the stem cells of the present invention may require specific environments for differentiation, which include the presence of a supporting scaffold (e.g. osteoblasts) The 3D scaffold provides a supporting frame and may act as a template for osteogenesis.

Differentiated embryonic stem cells of the present invention can be utilized in treating various disorders. For example, oligodendrocyte precursors can be used to treat myelin disorders (Repair of myelin disease: Strategies and progress in animal models. Molecular Medicine Today. 1997, 554-561), chondrocytes or mesenchymal cells can be used in treatment of bone and cartilage defects (U.S. Pat. No. 4,642,120) and cells of the epithelial lineage can be used in skin regeneration of a wound or burn (U.S. Pat. No. 5,716,411).

For certain disorders, such as genetic disorders in which a specific gene product is missing [e.g., lack of the CFTR gene-product in cystic fibrosis patients (Davies J C, 2002. New therapeutic approaches for cystic fibrosis lung disease. J. R. Soc. Med. 95 Suppl 41:58-67)], the embryonic stem cells of the present invention are preferably manipulated to over-express the mutated gene prior to their administration to the individual. It will be appreciated that for other disorders, the ESCs of the present invention should be manipulated to exclude certain genes.

Preferably, the embryonic stem cells of the present invention are at least partially differentiated prior to transformation as implantation of undifferentiated ES cells may lead to formation of benign teratomas in the recipients. This may be achieved by designing a transgenic methodology to eliminate residual minority stem cells from differentiated ES cell cultures, for example based on negative selection of Oct 4-expressing cells. Use of a positive selection transgene to achieve lineage-directed differentiation would also reduce the risk of tumor formation by selecting against the remaining undifferentiated, proliferating stem cell population.

The embryonic stem cells of the present invention may be genetically engineered (such as by using the above teachings) to reduce or eliminate immune-mediated rejection so that lifelong pharmacologic immunosuppression would not be required.

Homologous recombination has been used to "knock-out" major histocompatibility complex (MHC) class I and class II molecules in mouse ES cells [Grusby M J, et al., Proc Natl Acad Sci USA 1993; 90:3913-3917]. However, MHC class I- and class II-deficient skin grafts are still rejected, possibly on the basis of indirect allo-recognition-mediated rejection and/ or natural killer cell-mediated destruction [Grusby M J, et al., Proc Natl Acad Sci USA 1993; 90:3913-3917]. Thus, in addition to deleting foreign MHC genes, desired MHC genes may also be "knocked-in", so that ES cell-derivative transplants of the present invention are seen as "self" by the prospective recipient [Westphal C H, Leder P. Curr Biol 1997; 7:530-533]. Alternatively, genes for immunosuppressive molecules such as Fas-ligand could be inserted into the ES cells of the present invention, or important immune-stimulating proteins, such as B7 antigens or CD40-ligand, could be deleted from ES cells [Harlan D M, Kirk A D, JAMA 1999; 282:1076-1082]. Irrespective of the method used, the ability to stably integrate genetic modifications into ES cells provides an advantage over using adult somatic cells, which are less reliably genetically altered.

Nuclear transfer technology may provide a more precise means to prevent rejection of the transplanted ES cells of the present invention. This technique would lead to ES cell-derived cells that are an exact genetic match to the recipient. In this way, there would be minimal host immune response since all nuclear genes, including major and minor histocompatibility loci, would be seen as "self."

In this technique, a nucleus is extracted from a normal somatic cell of a patient, e.g. from a skin biopsy, and then injected into an enucleated oocyte. Oocyte cytoplasm has the ability to reprogram differentiated nuclei, and as such, would reestablish an embryonic gene expression program in the chromatin of the somatic cell nucleus. A delayed blastocyst developing from this oocyte would be a source for the derivation of a new ES cell line of the present invention, which would be genetically matched for each nuclear gene of the patient. In this setting, the potential immune-mediated destruction of the graft would be limited to minor antigen differences derived from mitochondrial genes or to autoimmune processes, such as diabetes. Combining nuclear transfer technology and ES cell derivation has been successfully achieved in cows and mice, in order to establish transgenic ES cell lines from reprogrammed somatic cell nuclei [First N L, Thomson J., Nat Biotechnol 1998; 16:620-621].

Establishing hematopoietic chimerism is another potential means of preventing rejection of the transplanted cells of the present invention. By using the same ES cell lines to derive both hematopoietic stem cells and other lineages, it may be possible to initially achieve hematopoietic chimerism followed by engraftment of a second cell type. The second lineage would not be rejected as it would be regarded as "self" by the chimeric patient's bone marrow and immune system, which were derived, in part, from the same ES cell line. No long-term treatment with potentially toxic drugs would then be required.

The embryonic stem cells of the present invention may be transplanted to a human subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the embryonic stem cells of the present invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

One may administer the pharmaceutical composition in a systemic manner (as detailed hereinabove). Alternatively, one may administer the pharmaceutical composition locally, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (nucleic acid construct) effective to prevent, alleviate or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

In addition to cell replacement therapy, the embryonic stem cells of the present invention can also be utilized to prepare a cDNA library. mRNA is prepared by standard techniques from the embryonic stem cells and is further reverse transcribed to form cDNA. The cDNA preparation can be subtracted with nucleotides from embryonic fibroblasts and other cells of undesired specificity, to produce a subtracted cDNA library by techniques known in the art.

The embryonic stem cells of the present invention can be used to screen for factors (such as small molecule drugs, peptides, polynucleotides, and the like) or conditions (such as culture conditions or manipulation) that affect the differentiation of lineage precursor to terminally differentiated cells. For example, growth affecting substances, toxins or potential differentiation factors can be tested by their addition to the culture medium.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Generation of Cell Lines Derived from Delayed Blastocyst Culture

Materials and Methods

Blastocyst cultivation: Discarded zygotes were donated by couples undergoing in vitro fertilization (IVF) treatment at Rambam Medical Center having signed consent forms approved by the national Helsinki committee. Zygotes were cultured to the blastocyst stage according to IVF laboratory standard protocol: drops under oil using specialized Cook media (Queensland, Australia) including insemination medium (OM), growth medium (GM) and blastocyst stage embryo medium (BM).

Derivation of extended blastocyst cell (EBC) lines: Following zona pellucida digestion by Tyrode's acidic solution (Sigma Aldrich, St Louis, Mo., USA) the exposed blastocysts were plated on mitotically inactivated mouse embryonic fibroblasts (MEFs). Eight attached blastocysts were cultured on MEFs as whole embryos for 9-14 days post fertilization until a large cyst developed. If needed, due to MEF quality, the embryos were transferred in whole to new MEF-covered plates using 27 gouge syringe needles, leaving a few of the surrounding fibroblasts behind. Following cyst development, a disc-like structure was isolated and plated separately on a fresh MEF-covered plate. Cells with stem cell morphology (small cells with large nucleus) were passaged mechanically. Following a few passages (4-6), when a homogonous culture was achieved, the cells were passaged routinely every four to six days using 1 mg/ml type IV collagenase (Gibco Invitrogen corporation products, San Diego, Calif., USA).

Culture media: For the derivation and initial passages, cells were grown in a culture medium consisting of 80% KO-DMEM and supplemented with 20% defined FBS (HyClone, Utah, USA), 1 mM L-glutamine, 0.1 mM $\beta$-mercaptoethanol, 1% non-essential amino acid stock (all from Gibco Invitrogen corporation products, San Diego, Calif., USA products).

The cells were then cultured using medium consisting of 85% ko-DMEM and supplemented with 15% ko-serum replacement, 1 mM L-glutamine, 0.1 mM $\beta$-mercaptoethanol, 1% non-essential amino acid stock and 4 ng/ml basic fibroblast growth factor (bFGF) (all products from Gibco Invitrogen corporation products, San Diego, Calif., USA). The cells were frozen in liquid nitrogen using a freezing solution consisting of 10% DMSO (Sigma, St Louis, Mo., USA), 10% FBS (Hyclone, Utah, USA) and 80% KO-DMEM.

Results

Figure 1E:
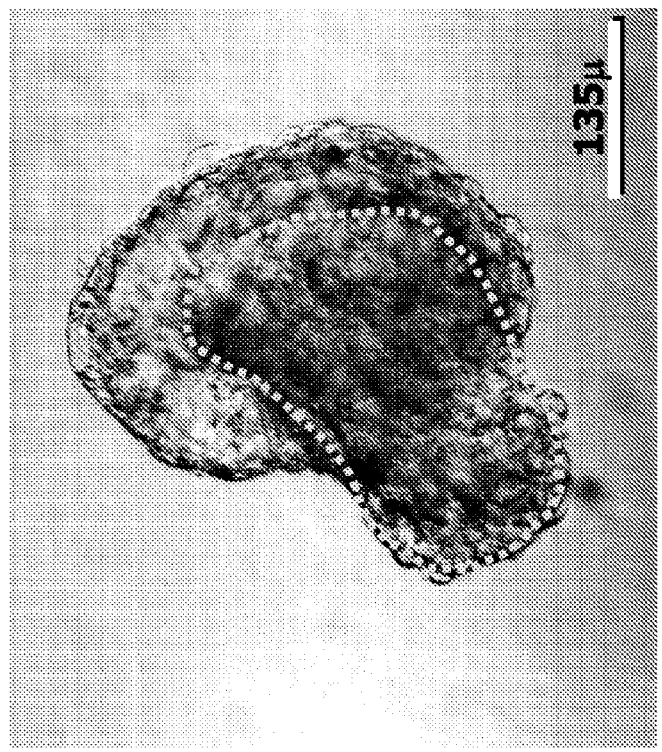

Four EBC lines were derived with the use of the extended blastocyst culture technique. Of the eight plated embryos, four had a surrounding monolayer of trophoblast or fibroblast cells, and the inner cell mass (ICM) started to grow as a monolayer, creating a typical ES cell colony following five to ten days (I-5, I-8, I-10, I-11). The other four embryos continued to develop in whole with a notable cyst and a disc-like area (see FIG. 1E) from which the EBC lines were derived (J2, J3, J6, J7). FIGS. 1A-D are photographs of light microscopy images depicting the generation of EBC J3. FIG. 1E is a light microscopy image of the EBC J6.

Example 2

Morphological Analysis of EBCs

Materials and Methods

Karyotype analysis: Cell division was blocked in mitotic metaphase using colcemid-spindle formation inhibitor (karyoMax colcemid solution, Gibco Invitrogen corporation products, San Diego, Calif., USA). Nuclear membranes were broken following hypotonic treatment. For chromosome visualization, G-band standard staining (Giemsa, Merck, Darmstadt, Germany) was performed. The karyotypes were analyzed and reported according to the "International System for Human Cytogenetic Nomenclature" (ISCN). At least 20 cells were examined from each cell line, 10 from each different sample. The samples were taken from the EBCs following at least 20 consecutive passages.

Microscopy: Light microscopy was performed to examine EBC colonies. Electron and monolayer microscopy were performed to examine histological sections of extended blastocyst and embryonic stem cells. The phase-contrast is Olympus CH30, the transmitted electron microscopy in use JEM-100sx (JEOL, Tokyo, Japan).

Results

Karyotype analysis revealed that two of the examined EBC lines comprised a normal 46, XY karyotype and two comprised a normal 46, XX karyotype. None of the 100 cells examined exhibited any karyotype abnormality. The karyotype analysis was carried out following at least 20 passages of continuous culture indicating that the cell lines possess a stable karyotype.

Light microscopy revealed that the colonies formed by the EBCs presented a similar morphology to that of hESC lines i.e. round colonies with spaces between the cells and relatively large nucleii with distinct nucleoli. However, when cell monolayers were examined under a light microscope, it was noted that while the cells inside the EBC colonies were organized as a columnar epithelium with somewhat smaller nucleii and villi throughout the upper side of the colony (FIGS. 2B-C), the ESC colonies were organized as stratified epithelium, with no villi facing the upper side (FIG. 2A). Furthermore, electron microscopy indicated that zonula occludente junctions, typical for columnar epithelium, could be detected between the EBCs and not between the upper rows of hESCs (FIGS. 2D-E). Other reports describe this morphology as the morphology of early differentiating hES cells [Sathananthan et aL 2002].

Example 3

Differentiational Analysis of EBCs Compared to ESCs

Materials and Methods

Immunostaining: EBCs and hESCs were fixed with 4% paraformaldehyde, and exposed to primary antibodies (1:50) overnight at 4° C. Cy3 conjugated antibodies (Chemicon International, Temecula Calif., USA) at a dilution of 1:100 were used as secondary antibodies in combination with all primary antibodies except Brachury where a FITZ conjugated secondary antibody was used (Santa Cruz). Stage-specific embryonic antigens (SSEA) 1,3 and 4 (Hybridoma bank, Iuwa, USA), tumor recognition antigens (TRA) 1-60 and TRA1-81, (Chemicon International, Temecula, Canada) Brachury and Oct4 (Santa Cruz) were used as primary antibodies. For double immunostaining, EBCs and hESCs were fixed with 4% paraformaldehyde, and exposed to Oct4 antibody (1:50) for 30 minutes at room temperature. Following washing, the fixed-cells were incubated for 30 minutes at room temperature with Brachury (1:50) antibody. This protocol was repeated with the secondary antibodies. For each of the reactions a negative control was used in which primary antibodies were not used.

Teratoma formation: $10^7$ cells in 100 μl culture medium were harvested and injected into the rear leg muscles of four-week-old male SCID-beige mice. The resulting teratomas were harvested 9 weeks (±2 days) post injection. Each teratoma was weighed, following which a portion of the tumours was collected for RNA isolation and another portion was fixed. The sections were fixed in 10% neutral-buffered formalin, dehydrated in graduated alcohol (70%-100%) and embedded in paraffin. For histological examination, 1-5 μm sections were deparafinized and stained with hematoxylin/eosin (H&E).

EB formation: For the formation of EBs, four to six confluent wells of a six-well plate (40-60 cm²) of EBCs and hESCs were used. The cells were removed from their culture dishes using 1 mg/ml type IV collagenase, further broken into small clumps using 1000 μl Gilson pipette tips, and cultured in suspension in 58 mm Petri dishes (Greiner, Germany). EBs were grown in suspension for five days in medium supplemented with 15% ko-serum replacement, with similar supplements as the continuous culture medium without the addition of bFGF. After five days in suspension, part of the EBs were trypsinized, further broken up using 1000 μl Gilson pipette tips, and plated on gelatine-coated culture plates. The EB-derived cells were further cultured in medium supplemented with FBS (Hyclone, Utah, USA) for ten to eleven additional days. Both samples of the EBs cultured in suspension and the plated EB-derived cells were collected for RNA isolation.

RT-PCR reaction: Total RNA was isolated from EBCs, five day-old EBs cultured in suspension, plated EB-derived cells and teratoma sections using Tri-Reagent (Sigma Aldrich, St. Louis, Mo., USA), according to the manufacturer's recommended protocol. cDNA was synthesized from 1 μg total RNA using MMLV reverse transcriptase RNase H minus (Promega, Madison, Wis., USA). PCR reactions comprised denaturation for 5 minutes in 94° C. followed by repeated cycles of 30 seconds at 94° C., at the annealing temperature (as in Table 2) and for extension at 72° C. PCR primers and reaction conditions used are as described in Table 2 herein below. PCR products were size fractionated using 2% agarose gel electrophoresis, following staining with ethidium bromide. RT reaction mixture was used as a negative control, and the β-actin gene (a house-keeping gene) was used for normalization.

TABLE 2

| Gene | Product size bp | 5' primer SEQ ID NO: | 3' primer SEQ ID NO: | Mg mM | Annealing temp | Ref. |
|---|---|---|---|---|---|---|
| Undifferentiated markers and receptors | | | | | | |
| Epidermal growth factor receptor 1 (EGFR) U48727 U48728 | 300 | CAGTCGTCAGCC TGAACATAACAT CC SEQ ID NO: 1 | AGGTTGCACTTG TCCACGCATTCC C SEQ ID NO: 2 | 1.5 | 65, AM5 | Schuldiner et al PNAS 2000 |
| Activin receptor β2 (ACTR) AF060200 | 550 | ACACGGGAGTGC ATCTACTACAAC G SEQ ID NO: 3 | TTCATGAGCTGG GCCTTCCAGACA C SEQ ID NO: 4 | 1.5 | 65, AM5 | Schuldiner et al PNAS 2000 |
| Octamer binding | 219 | GAGAACAATGAG AACCTTCAGGAG | TTCTGGCGCCGG TTACAGAACCA | 1.5 | 55, DK4 | Abdel-Rahman et al. Hum reprod 1995 |

TABLE 2-continued

| Gene | Product size bp | 5' primer SEQ ID NO: | 3' primer SEQ ID NO: | Mg mM | Annealing temp | Ref. |
|---|---|---|---|---|---|---|
| protein 4 (Oct4) NM_000270 | | A SEQ ID NO: 5 | SEQ ID NO: 6 | | | |
| Nanog NG_004095 | 800 | ACTAACATGAGT GTGGATCC SEQ ID NO: 7 | TCATCTTCACAC GTCTTCAG SEQ ID NO: 8 | 1.5 | 61, AM1 | Daheron et al Stem Cells.2004 |
| LIF X13967 | 560 | CAGCATCACTGA ATCACAGAGC SEQ ID NO: 9 | AGTATGAAACAT CCCCACAGGG SEQ ID NO: 10 | 1.5 | 61, AM1 | Chen et al. Fer Ster 1999. |
| LIF-R NM_002310 | 459 | CAAAAGAGTGTC TGTGAG SEQ ID NO: 11 | CCATGTATTTAC AATTGGC SEQ ID NO: 12 | 1.5 | 61, AM1 | Chen et al. Fer Ster 1999. |
| Rex1 AF450454 | 306 | GCGTACGCAAAT TAAAGTCCAGA SEQ ID NO: 13 | CAGCATCCTAAA CAGCTCGCAGAA T SEQ ID NO: 14 | 1.5 | 56, 3AM | Henderson et al. Stem Cells 2002. |
| FGF4 NM_002007 | 370 | CTACAACGCCTA CGAGTCCTACA SEQ ID NO: 15 | GTTGCACCAGAA AAGTCAGAGTTG SEQ ID NO: 16 | 1.5 | 52, 4AM | Henderson et al. Stem Cells 2002. |
| FGF5 NM_004464 | 550 | CACTGATAGGAA CCCTAGAGG SEQ ID NO: 17 | CTCCGACTGCTT GAATCTTGG SEQ ID NO: 18 | 1.5 | 65, AM5 | Crickard et al Gynecology Oncology 1994 |
| Sox2 Z31560 | 448 | CCCCCGGCGGCA ATAGCA SEQ ID NO: 19 | TCGGCGCCGGGG AGATACAT SEQ ID NO: 20 | 1.5 | 60, DK5 | Henderson et al. Stem Cells 2002. |
| β-Actin NM_001101 | 838 | ATCTGGCACCAC ACCTTCTACAAT GAGCTGCG SEQ ID NO: 21 | CGTCATACTCCT GCTTGCTGATCC ACATCTGC SEQ ID NO: 22 | 1.5 | 62 | Henderson et al. Stem Cells 2002. |
| Retinoic Acid Receptor type alpha (RAR) AH007261 | 500 | AGCAGCAGTTCT GAAGAGATAGTG CC SEQ ID NO: 23 | GTGGAGAGTTCA CTGAACTTGTCC C SEQ ID NO: 24 | 1.5 | 65, AM5 | Schuldiner et al PNAS 2000 |
| Fibroblast Growth Factor Receptor type I (FGFRI) M34641 | 410 | AGCATCATAATG GACTCTGTGGTG CC SEQ ID NO: 25 | AGTCCGATAGAG TTACCCGCCAAG C SEQ ID NO: 26 | 1.5 | 65, AM5 | Schuldiner et al PNAS 2000 |
| Bone Morphogenic Protein 4 Receptor type II (BMP4RII) D50516 | 800 | TCTGCAGCTAGG TCCTCTCATCAG C SEQ ID NO: 27 | TATACTGCTCCA TATCGACCTCGG C SEQ ID NO: 28 | 1.5 | 65, AM5 | Schuldiner et al PNAS 2000 |
| Hepatocyte Growth Factor Receptor (c-Met) AC002080 | 440 | AGAAATTCATCA GGCTGTGAAGCG CG SEQ ID NO: 29 | TTCCTCCGATCG CACACATTTGTC G SEQ ID NO: 30 | 1.5 | 65, AM5 | Schuldiner et al PNAS 2000 |
| Nerve Growth Factor Receptor (NGFR) AC006487 | 410 | TGTTCTCCTGCC AGGACAAGCAGA AC SEQ ID NO: 31 | TCTTGAAGGCTA TGTAGGCCACAA GG SEQ ID NO: 32 | 1.5 | 65, AM5 | Schuldiner et al PNAS 2000 |

TABLE 2-continued

| Gene | Product size bp | 5' primer SEQ ID NO: | 3' primer SEQ ID NO: | Mg mM | Annealing temp | Ref. |
|---|---|---|---|---|---|---|
| Transforming Growth Factor Receptor type II (TGFRII) AH004921 | 530 | TAGTCACTGACA ACAACGGTGCAG TC SEQ ID NO: 33 | ACAGTGCTCGTC GCTGAACTCCAT GAGC SEQ ID NO: 34 | 1.5 | 65, AM5 | Schuldiner et al PNAS 2000 |
| Mesodermal markers | | | | | | |
| β-Globulin V00499 | 410 | ACCCTGACTCCT GAGGAGAAGTCT GC SEQ ID NO: 35 | TAGCCACACCAG CCACCACTTTCT G SEQ ID NO: 36 | 1.5 | 65, AM5 | Schuldiner et al PNAS 2000 |
| Collagen type 1 α 1 (cartiladge) Z74615 | 180 | CGATGGCTGCAC GAGTCACAC SEQ ID NO: 37 | CAGGTTGGGATG GAGGGAGTTTAC SEQ ID NO: 38 | 1.5 | 64, AM7 | B. Schmitt et al Differentiation 2003 |
| Collagen type 2 α 1 (cartiladge) X06268 | 128 | CCGGGCAGAGGG CAATAGCAGGTT SEQ ID NO: 39 | CAATGATGGGGA GGCGTGAG SEQ ID NO: 40 | 1.5 | 64, AM7 | B. Schmitt et al Differentiation 2003 |
| Cartilage oligomeric matrix protein (comp) L32137 | 116 | GGGTGGCCGCCT GGGGGTCTT SEQ ID NO: 41 | CTTGCCGCAGCT GATGGGTCTC SEQ ID NO: 42 | 1.5 | 64, AM7 | B. Schmitt et all Differentiation 2003 |
| Cartilage link protein U43328 | 145 | GCGTCCGCTACC CCATCTCTA SEQ ID NO: 43 | GCGCTCTAAGGG CACATTCAGTT SEQ ID NO: 44 | 1.5 | 64, AM7 | B. Schmitt et al Differentiation 2003 |
| Aggrecan (cartilage) X17406 | 146 | CCAGTGCACAGA GGGGTTTG SEQ ID NO: 45 | TCCGAGGGTGCC GTGAG SEQ ID NO: 46 | 1.5 | 64, AM7 | B. Schmitt et al Differentiation 2003 |
| Brachyury NM003181 | 250 | TAAGGTGGATCT TCAGGTAGC SEQ ID NO: 47 | CATCTCATTGGT GAGCTCCCT SEQ ID NO: 48 | 2.5 | 65 AM5 | P. J. Gokhale et al. Cell Growth Differ. 2000. |
| Cardiac Actin (cACT) NM_005159 | 630 | TCTATGAGGGCT ACGCTTTG SEQ ID NO: 49 | CCTGACTGGAAG GTAGATGG SEQ ID NO: 50 | 1.5 | 65 AM5 | Schuldiner et al PNAS 2000 |
| δ-Globin (δ-Glob) V00505 | 430 | ACCATGGTGCAT CTGACTCCTGAG G SEQ ID NO: 51 | ACTTGTGAGCCA AGGCATTAGCCA C SEQ ID NO: 52 | 1.5 | 65 AM5 | Schuldiner et al PNAS 2000 |
| Renin AH007216 | 590 | AGTCGTCTTTGA CACTGGTTCGTC C SEQ ID NO: 53 | GGTAGAACCTGA GATGTAGGATGC SEQ ID NO: 54 | 1.5 | 65 AM5 | Schuldiner et al PNAS 2000 |
| GATA4 transcription factor D78260 | 475 | AGACATCGCACT GACTGAGAAC SEQ ID NO: 55 | GACGGGTCACTA TCTGTGCAAC SEQ ID NO: 56 | 1 | 60, DK5 | Home Made |
| IL-6 NM_00060 | 628 | ATGAACTCCTTC TCCACAAGCGC SEQ ID NO: 57 | GAAGAGCCCTCA GGCTGGACTG SEQ ID NO: 58 | 1.5 | 54.2 | Gutsche et al. Mol Human Reproduction 2003 |
| BMP2 NM_001200 | 200 | TCAAGCCAAACA CAAACAGC SEQ ID NO: 59 | ACGTCTGAACAA TGGCATGA SEQ ID NO: 60 | 1.5 | 61, DK3 | Bunger et al. Calcif Tissue Int.2003 |
| BMP4 D30751 | 378 | GCCGGAGGGCCA AGCGTAGCCCTA AG | CTGCCTGATCTC AGCGGCACCCAC ATC | 1.5 | 64.7, DK2 | Bae et al. Toxicological Sciences 2003 |

TABLE 2-continued

| Gene | Product size bp | 5' primer SEQ ID NO: | 3' primer SEQ ID NO: | Mg mM | Annealing temp | Ref. |
|---|---|---|---|---|---|---|
| | | SEQ ID NO: 61 | SEQ ID NO: 62 | | | |
| CD44 M59040 | 200 | CCAACACCTCCC ACTATGAC SEQ ID NO: 63 | TATACTCGCCCT TCTTGCTG SEQ ID NO: 64 | 1.5 | 61, DK3 | Ramos-Nino et al. Cancer Research 2003 |
| Endodermal markers | | | | | | |
| Amylase M24895 | 490 | GCTGGGCTCAGT ATTCCCCAAATA C SEQ ID NO: 65 | GACGACAATCTC TGACCTGAGTAG G SEQ ID NO: 66 | 1.5 | 65, AM5 | Schuldiner et al PNAS 2000 |
| α1 Anti trypsin K02212 | 360 | AGACCCTTTGAA GTCAAGGACACC G SEQ ID NO: 67 | CCATTGCTGAAG ACCTTAGTGATG C SEQ ID NO: 68 | 1.5 | 65, AM5 | Schuldiner et al PNAS 2000 |
| Albumin M12533 | 450 | CCTTTGGCACAA TGAAGTGGGTAA CC SEQ ID NO: 69 | CAGCAGTCAGCC ATTTCACCATAG G SEQ ID NO: 70 | 1.5 | 65, AM5 | Schuldiner et al PNAS 2000 |
| Glucagon X03991 | 370 | CTCAGTGATCCT GATCAGATGAAC G SEQ ID NO: 71 | AGTCCCTGGCGG CAAGATTATCAA G SEQ ID NO: 72 | 1.5 | 65, AM5 | Schuldiner et al PNAS 2000 |
| α-Phetoprotein BC027881 | 216 | GCTGGATTGTCT GCAGGATGGGGA A SEQ ID NO: 73 | TCCCCTGAAGAA AATTGGTTAAAA T SEQ ID NO: 74 | 1.5 | 60, DK5 | Home Made |
| GnRH | 219 | TCAAAAACTCCT AGCTGGCCT SEQ ID NO: 75 | CTTTCCAGAGCT CCTTTCAGGT SEQ ID NO: 76 | 1.5 | 55, DK4 | |
| CG | 556 | GCAGCTATCTTT CTGGTCACAT SEQ ID NO: 77 | ACTCTGAGGTGA CGTTCTTTTG SEQ ID NO: 78 | 2.0 | 60, DK5 | |
| Ectodermal marker | | | | | | |
| Neurofilament heavy Chain (NFH) X15307 X15309 | 400 | TGAACACAGACG CTATGCGCTCAG SEQ ID NO: 79 | CACCTTTATGTG AGTGGACACAGA G SEQ ID NO: 80 | 1.5 | 65, AM5 | Schuldiner et al PNAS 2000 |

Chip DNA analysis: Samples of RNA were isolated from confluent cultures of undifferentiated hESCs and EBCs cultured as described in Example 1 with mitotically inactivated MEFs. RNA isolation was conducted as described hereinabove for RT-PCR analysis. Four commercial gene array membranes were used: human stem cell genes, human TGF$_\beta$/BMP pathway genes, human neurotrophin and receptor genes and extracellular molecules genes (all non-radioactive from GEarray Q series, numbers, HS-018, respectively, SuperArrays Biosciences Inc., Frederick, Md., USA). The analysis was performed according to the supplier's instructions. In brief, for RT reaction 200U Maloney murine leukaemia virus-derived reverse transcriptase was used (Promega, Madisom, Wis., USA). The array membranes were hybridized overnight with biotin-labelled probes at 60° C., washed twice at 60° C. for 15 minutes with 2×SSC/1% SDS followed with 0.1×SSC/1% SDS. The detection stage comprised a 30-minute incubation of the membranes with alkaline phosphatase-conjugated streptavidin followed by a five-minute incubation with CDP-star substrate at room temperature. The membranes were exposed to X-ray film. The quantification of the gene expression was carried out using GEarray analyzer and Scanalyze software.

Real time PCR analysis: cDNA was synthesized as described above for the RT-PCR reaction. Taq-Man Universal PCR master Mix and Assay-on-Demand gene expression Probes for Oct 4 and β-Actin were used according to the manufacturer instructions (Applied Biosystems, Foster City, Calif.). The real time PCR reaction was performed using Applied Biosystem 7000 DNA Sequence Detection system, according to the manufacturer guidelines (Applied Biosystems, Foster City, Calif.). The relative expression of Oct 4 was normalized according to the β-Actin expression in cDNA isolated from the same sample, by using the standard curve method described by the manufacturer. To calculate differences in Oct 4 amplification between the various tested cell lines, a relative standard curve method was used (Applied Biosystems, Foster City, Calif.). The data was collected from three different samples for each line (I3, I6, J3, J6) and each cDNA sample was assayed at least twice, averaged and graphed with standard deviations.

Affymetrix chip analysis: RNA was isolated from undifferentiated I3 cells at passage 45, from I6 cells at passage 42, from J3 cells at passage 37 and from J6 cells at passage 49 following culture on MEFs. RNA integrity was passed by gel electophoresis. Total RNA samples were concentrated at 1 µg/µl, cleaned with Phenol/chlorophorm/Isoamyl alcohol in Phase lock gel (PLG) tubes (Invitrogen Corporation, San Diego, Calif., USA). 10 µg of each sample was used to prepare biotinylated target cDNA and hybridised to Affymetric focus gene chips according to the manufacturer's instructions. The microarray was scanned by Affymetric scanner (Affymetrix, Santa Clara, Calif., USA). For bioinformatics the MAS 5.0 Affymetrix array analysis software was used. Expression levels of greater than 3 fold were considered relevant. The p-value of each spot was calculated using Anove tests, each SP was centered and normalized. For clustering analysis, the super Paramagnetic Clustering Method was used. David software was used for the Go-Chart analysis.

Illumina beadarray analysis: RNA was isolated from undifferentiated J3 and from hESC as described hereinabove for Affymetrix chip analysis. For gene profiling Illumina Beadarray was used (Sentrix human Expression BeadChip, Illumina, San Diego, Calif., USA).

2-D gel protein electrophoresis analysis: The proteins were dissolved in 150 µl running buffer consisting of: 7M urea, 2M thiourea, 2% w/v CHAPS, 65 mM DTT and 1.25% v/v ampholyte and 3 β1 Bromo-Phenol-Blue (BPB). The protein levels were measured using the Bradford method. 200 µg of protein were loaded on each strip (BioRad, 3-10 NL, Immobiline DryStrips, 11 cm) and rehydrated for one hour without voltage and subsequently 12 hours in 50 mV. The isoelectric focusing was conducted as follows: one hour in 200 V, 500 V, 1000 V respectively followed by 30 minutes of increased voltage up to 8000 V, where it remained until reaching 69,145 VH on VH (Volt Hours).

Each strip underwent equilibration in 50 mg DTT dissolved in equilibration buffer containing: 6 M Urea, 30% w/v glycerol and 2% SDS in 0.05 M Tris-HCl buffer (1.5 M Tris-HCl and 0.4% w/v SDS), pH 8.8 10 µl BPB, for 15 minutes. The second stage of the equilibration was conducted in 200 mg Iodoacetamide (IAA) dissolved in equilibration buffer and 10 µl BPB, for 15 minutes. The strip were than loaded onto Bio Rad gradient gels (4-20%). A dual color marker was used to evaluate the molecular level. Electrophoresis was conducted for one hour at 200 V. The resultant gels were stained with SeeBand forte (GeBA) according to the manufacturer's instructions. The gels were scanned using Bio Rad Fluor-S scanner, and analyzed using Bio Rad PDQUEST 7.0.1 software.

Osteoblast differentiation: hESC (I4 and I6) and EBC cells (J3 and J6) were cultured on stromal cell matrix (ATCC no. SR4987) in medium consisting of 85% MEM alpha, 0.5% Penicillin streptomycin, 0.2% Ribnucleosides & Deoxyribnucleosides (Biological Industries, Bait Haemek, Israel), 15% FBS (HyClone, Utah, USA), 0.05 mg/ml Ascorbic Acid, 1% β-glycophosphate (Sigma, St. Louis, USA). Following 5 days of co-culture, EBs were formed as described above and cultured in suspension in the identical medium for an additional 5-7 days. The EBs were then dissociated using trypsin-EDTA solution, and re-plated on stromal cell matrix. Following one week, the cells were stained with Alizarin Red (Fluka, Bochs, Switzerland) to identify calcium secretion.

Results:

Based on the morphology of the colonies, it was noted that the background differentiation of the EBCs is higher than that in the regular hESCs. A consistent background differentiation of more than 15% could be detected in the J2 and J6 cell lines. A single-cell clone of the J2 line, J2.1, expressed the same percentage of background differentiation as the parental cell line. The J3 differentiation rates were found to be similar to those of hESCs.

Similar to hESCs, immunostaining of EBCs with embryonic stage-specific markers revealed strong staining with SSEA4 and TRA-1-60, no staining with SSEA1 and weak staining with SSEA3. Unlike hESC, the EBC lines demonstrated weak staining with TRA-1-81 (FIGS. 3A-G).

Figure 6:
FIG. 6 is a photograph of a teratoma section of an EBD line stained with H&E showing cartilage and bone tissue as observed under a light microscope. The teratoma was generated following introduction of cells from J6 cell lines into four-week-old male SCID-beige mice. Hoffman resolution bar=20 µM.

The teratoma model was used to test the EBC pluripotency. The cells were injected into the hind limb muscles of four-week-old male SCID-beige mice, similar to the method used to assess the pluripotency of hESCs. During the first set of experiments approximately five million cells were injected into each mouse with at least four mice per cell line. This showed a reduced success rate of 30% for the EBCs and a 100% success rate for the hESCs. In order to efficiently compare the pluripotency of the different types of cell lines, the number of injected cells was doubled to ten million per mouse. In this case, 11 of 12 EBC-injected mice resulted in teratomas. The size of the teratomas differed between the two types of cell lines as measured by the tumor weight; specifically the average weight of the hESC-resulting teratomas was 9.4 gr (N=8) and the average weight of the EBC-resulting teratomas was only 3.5 gr (N=12). In addition to the difference in size, the EBC-resulting teratomas contained a limited number of ectoderm and endoderm representative tissues and had a more distinct appearance of mesodermal tissues (FIGS. 4A-B). In one case, the J2 resultant teratoma did not contain any ectodermal tissues (one mouse out of three examined). While screening several teratoma sections, a tissue representative for all three embryonic germ layers could be found (FIGS. 5A-F). In the J6 teratomas, a predominance of cartilage tissues was observed (FIG. 6).

The results from the teratoma experiments give the impression that the EBCs have a higher tendency to differentiate into mesenchymal tissue than hESCs. To further confirm this assumption, an in vitro differentiation model was used. Cells from both types were cultured in suspension for 5 days. The resultant EBs were broken into single cells, plated and further cultured for ten additional days as monolayer of differentiating cells. The expression of several genes was compared by RT-PCR between the different cell lines at different differentiation stages.

Several differences between the EBCs and the ESCs were detected in the non-differentiated cells. While the EBCs expressed undifferentiated markers such as OCT4, Nanog, Rex 1 and SOX2, they also expressed some early markers of cartilage differentiation such as COMP, cartilage linked protein and Aggrecan. The hESCs did not express as many differentiation markers at the undifferentiated stage. Another difference was the expression of STAT3 which was highly expressed by the EBCs but was low or non-existent in the hESCs. The results are summarized in Table 3 below.

TABLE 3

|  | Undifferentiated cells | | | | | |
|  | I series | | | J series | | |
| Gene | H9 | I6 | I3 | J3 | J6 | J2 |
| Mesodermal differentiation markers | | | | | | |
| β-Globulin | − | + | + | + | − | − |
| Collagen type I | − | + | + | + | + | + |
| COMP (Cartilage) | −− | −− | −− | +− | ++ | ++ |

TABLE 3-continued

|  | Undifferentiated cells | | | | | |
| --- | --- | --- | --- | --- | --- | --- |
|  | I series | | | J series | | |
| Gene | H9 | I6 | I3 | J3 | J6 | J2 |
| Collagen type II | − | − | − | + | + | + |
| Cartilage link protein | − | − | − | + | + | + |
| Aggrecan | − | − | − | + | + | + |
| Cardiac actin (cACT) | − | − | + | + | + | + |
| δ-Globulin | + | − | + | − | − | − |
| Renin | + | − | + | + | + | + |
| Brachychyury | −− | −− | −− | −+ | ++ | ++ |
| BMP 4 | − | − | − | + | + | + |
| BMP2 | −+ | −+ | −+ | ++ | ++ | ++ |
| Endodermal differentiation markers | | | | | | |
| Amylase | + | + | + | − | + | − |
| α1 Anti trypsin | + | − | + | + | + | + |
| Albumin | + | + | + | − | − | − |
| Glucagon | − | − | − | − | − | − |
| GnRH | + | + | + | + | + | + |
| CGα | + | + | + | − | − | + |
| Ectodermal differentiation marker | | | | | | |
| Neurofilament heavy chain (NFH) | − | − | + | + | + | + |
| Undifferentiated cell markers and receptors | | | | | | |
| Epidermal GF receptor I (EGERI) | ++ | ++ | ++ | +− | ++ | ++ |
| Activin receptor β2 | − | − | − | + | + | + |
| Retinoic acid receptor type α (RAR) | + | + | + | + | + | + |
| Fibroblast GF receptor (FGFRI) | + | + | + | + | + | + |
| BMP4RII | + | − | − | + | + | − |
| Hepatocyte GF receptor C-Met | + | + | + | + | + | + |
| Nerve GF receptor NGFR | − | − | − | + | + | + |
| Transforming GF receptor II (TGF) | + | + | + | + | + | + |
| Oct 4 | + | + | + | + | + | + |
| Rex 1 | ++ | ++ | ++ | ++ | ++ | ++ |
| Nanong | +++ | +++ | +++ | ++− | ±++ | ++− |
| FGF4 | ++− | ++− | +++ | −−− | −+− | +++ |
| Sox2 | −++ | +−+ | +++ | +++ | +++ | −++ |

Figure 7:
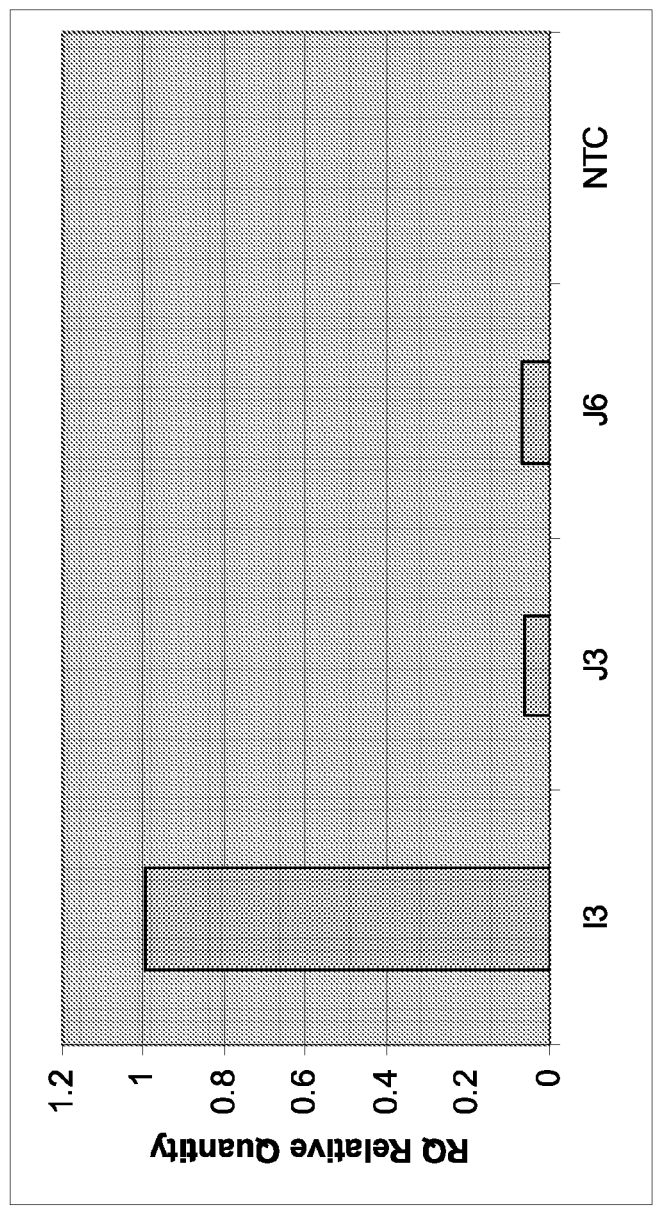
FIG. 7 is a bar graph depicting the relative expression of Oct 4 according to quantitative real-time PCR analysis in I3, J3 and J6 cell line. NTC=no template control, i.e. samples where no cDNA was added. I3 was used as the calibrator=1 (100%).
Figure 8A:
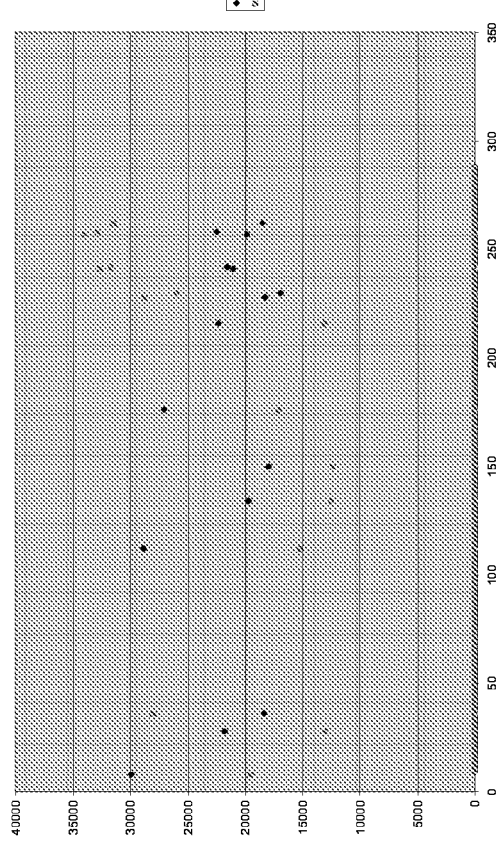
FIGS. 8A-D are dot graphs and photographs from chip DNA analysis of the GEarray S series stem cells genes, Hs601.2.
Figure 8B:
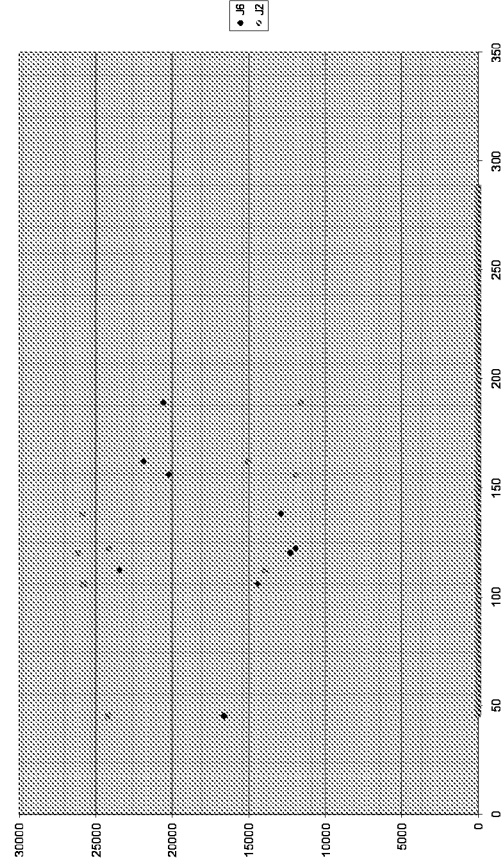
Figure 8C:
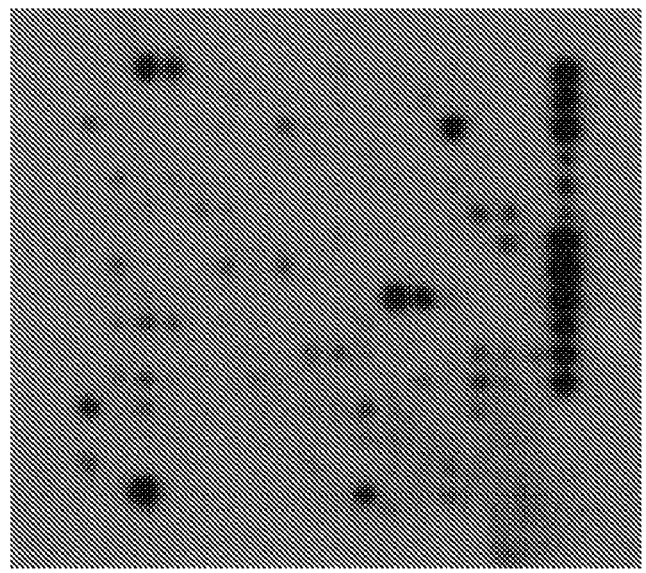
Figure 8D:
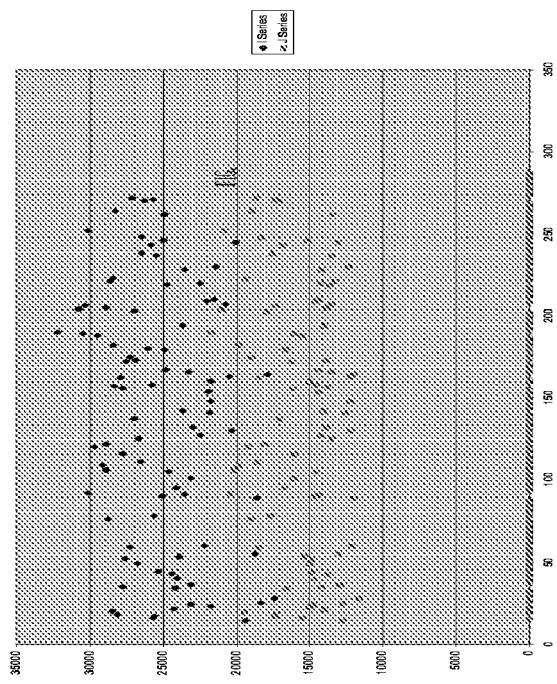

To evaluate possible differences in Oct 4 expression between EBCs and hESCs, a real time PCR analysis was conducted. Although the RT-PCR reaction revealed a clear band for Oct 4 expression for the EBC cells, according to quantitative real-time PCR analysis the levels of Oct 4 expression in these cells is significantly lower compared with hESCs (FIG. 7).

To allow a wider comparison between the two cell types, commercial DNA chip analysis was performed using an array of 288 "stem cells genes" (FIGS. 8A-D). When the number of genes with significant expression differences between two different HESC lines and two separate EBC lines were compared, only minor differences were found of 15 and 9 genes, respectively. When the genes' expression pattern was compared between the average of the EBC lines and HESC lines, 90 genes demonstrated different expression levels. Most of these genes had statistically higher expression in the EBCs—these genes are summarized in Table 4 hereinbelow.

TABLE 4

|  | I series | | | J series | | | Confirmed by |
| --- | --- | --- | --- | --- | --- | --- | --- |
| Gene | I6 | I3 | H9 | J2 | J6 | J3 | RT-PCR |
| Bone morphogenetic protein 2 (BMP2) NM_001200 | +− | ND | +− | ++ | ++ | ND | + |
| Bone morphogenetic protein 4 (BMP4) NM_001200 | − | ND | − | + | + | ND | + |
| CD44 Antigen M59040 | − | ND | − | + | + | ND | + |
| Cadherin 3 placental (CDH3) NM_001793 | −+ | ND | −+ | ++ | ++ | ND | |
| GATA4 transcription factor D78260 | − | ND | − | + | + | ND | + |
| Growth differentiation factor 3 (GDF3) NM_020634 | − | ND | − | + | + | ND | |
| Interleukin 6 (IL6) NM_00060 | − | ND | − | + | + | ND | + |
| Integrin beta 5 (ITGB5) NM_002213 | − | ND | − | + | + | ND | |
| Leukemia inhibitory factor (LIF) X13967 | − | ND | − | + | + | ND | + |
| Nerve growth factor beta polypeptide (NGFB) X52599 | − | ND | − | + | + | ND | |
| NK2 homolog B (NKX2B) NM_002509 | − | ND | − | + | + | ND | |
| Hypothetical protein (FLJ10314) BC039861 | −+ | ND | −+ | ++ | ++ | ND | |
| Noggin (NOG) NM_005450 | − | ND | − | + | + | ND | |
| Notch homolog 1translesion associated (NOTCH1) AF308602 | | ND | | + | + | ND | |
| Patched homolog (PTCH) U43148 | − | ND | − | + | + | ND | |
| Sox 13 SRY box 13 (SOX13) NM_005686 | − | ND | − | + | + | ND | |
| Sox18 SRY box 18 (Sox 18) NM_018419 | − | ND | − | + | + | ND | |
| Sox 2 SRY box 2 (Sox 2) BC013923 | − | ND | −+ | + | + | ND | −+ |
| Transforming growth factor beta receptor III (TGFBR3) NM_003243 | −+ | ND | −+ | ++ | ++ | ND | |
| THY-1 cell surface antigen (THY1) NM_006288 | − | ND | − | ++ | ++ | ND | |
| Undifferentiated embryonic cell transcription factor 1 (UTF1) NM_003577 | − | ND | − | + | −+ | ND | |
| Wingless-type MMTV integration family 6 (WNT6) NM_006522 | − | ND | − | + | + | ND | |
| Zinc finger protein 42 (ZFP42) AK056719 | − | ND | − | + | + | ND | |

Among these genes it was found that BMP2 expression was higher in the undifferentiated EBCs and mesenchymal markers such as BMP4, CD44, GATA4 (known also as early endodermal marker) were expressed by the two examined EBC lines. The expression of these genes was further confirmed by RT-PCR.

Table 5 below summarizes the results of TGF$_\beta$ related gene expression as analyzed by chip analysis.

TABLE 5

| Gene | I series | | | J series | | | Confirmed by RT-PCR |
|---|---|---|---|---|---|---|---|
| | I6 | I3 | H9 | J2 | J6 | J3 | |
| Bone morphogenetic protein 2 (BMP2) NM_001200 | − | ND | ND | ND | +/− | ND | + |
| Bone morphogenetic protein 4 (BMP4) NM_001200 | − | ND | ND | ND | ++ | ND | + |
| Anti Mullerian hormone (AMH) NM_000479 | −/+ | ND | ND | ND | ++ | ND | |
| Anti Mullerian hormone receptor type II (AMHR2) NM_020547 | + | ND | ND | ND | + | ND | |
| Bone morphogenetic protein 6 (BMP6) NM_001718 | − | ND | ND | ND | + | ND | |
| Bone morphogenetic protein receptor type IA (BMPR1A) NM_004329 | − | ND | ND | ND | +/− | ND | |
| Bone morphogenetic protein receptor type 2 (BMPR2) Z48923 | − | ND | ND | ND | +/− | ND | |
| Cyclin dependent kinase inhibitor 1A (CDKN1A) L47233 | −/+ | ND | ND | ND | + | ND | |
| Cerberus 1 (CER1) NM_005454 | ++ | ND | ND | ND | ++ | ND | |
| Collagen type I alpha2 (COL1A2) NM_000089 | ++ | ND | ND | ND | ++ | ND | |
| Collagen type III alpha1 (COL3A1) NM_000090 | ++ | ND | ND | ND | ++ | ND | |
| Distal-less homeo box 2 (DLX2) NM_004405 | − | ND | ND | ND | ++ | ND | |
| Lefty A (endometrial bleeding associated factor) (EBAF) NM_003240 | +++ | ND | ND | ND | +++ | ND | |
| Bone morphogenetic protein 9 = growth differentiation factor 2 (BMP9) AF188285 | ++ | ND | ND | ND | ++ | ND | |
| Growth differentiation factor 5 (GDF5, = cartilage derived morphogenetic protein 1) NM_000557 | − | ND | ND | ND | + | ND | |
| DNA-binding protein inhibitor ID-1 (ID1) D13889 | −/+ | ND | ND | ND | ++ | ND | |
| Inhibitor of DNA binding 2, dominant negative helix-loop-helix protein (ID2) D13891 | + | ND | ND | ND | +++ | ND | |
| Inhibitor of DNA binding 3, dominant negative helix-loop-helix protein (ID3) X66924 | −/+ | ND | ND | ND | ++ | ND | |
| Inhibitor of DNA binding 4, dominant negative helix-loop-helix protein (ID4) NM_001546 | +++ | ND | ND | ND | +++ | ND | |
| Inhibin α (INHA) NM_002191 | +++ | ND | ND | ND | +++ | ND | |
| Jun B proto-oncogene (JUNB) X51345 | + | ND | ND | ND | + | ND | |
| Lefty B (LEFTS) NM_020997 | +++ | ND | ND | ND | +++ | ND | |
| MAD homolog 2 (MADH2) NM_005901 | −/+ | ND | ND | ND | ++ | ND | |
| MAD homolog 3 (Smad 3) NM_005902 | −/+ | ND | ND | ND | ++ | ND | |
| MAD homolog 6 (Smad 6) NM_005585 | ++ | ND | ND | ND | ++ | ND | |
| v-myc avian myelocytomatosis viral oncogene homolog (c-myc) X00364 | − | ND | ND | ND | ++ | ND | |
| Runt-related transcription factor 2 (RUNX2) L40992 | ++ | ND | ND | ND | ++ | ND | |
| Plasminogen activator inhibitor type I (SERPINE1) M16006 | +++ | ND | ND | ND | +++ | ND | |
| Homo sapiens teratocarcinoma-derived growth factor 1 (TDGF1) NM_003212 | −/+ | ND | ND | ND | + | ND | |
| Transforming growth factor beta 1 (TGF$_{\beta1}$) X02812 | −/+ | ND | ND | ND | +++ | ND | |
| TGF$_\beta$ induced factor (TGIF) NM_003244 | − | ND | ND | ND | ++ | ND | |
| Tissue inhibitor of metalloproteinase 1 (TINP1) (erythroid potentiating activity, collagenase inhibitor) NM_003254 | − | ND | ND | ND | ++ | ND | |
| Transforming growth factor beta stimulated protein (TSC22) NM_006022 | − | ND | ND | ND | ++ | ND | |

Table 6 summarizes the data accumulated following chip analysis of all Extracellular Matrix related genes.

TABLE 6

| Gene | I series | | | J series | | | Confirmed by RT-PCR |
| --- | --- | --- | --- | --- | --- | --- | --- |
| | I6 | I3 | H9 | J6 | J2 | J3 | |
| Caveolin 1, Cavaolae protein 22 KD (CAV1) NM_001753 | + | ND | ND | + | ND | ND | |
| Cadherin 1, Type 1 epithelial Cadherin (CDH1) Z13009 | ++ | ND | ND | ++ | ND | ND | |
| Carcinoembryonic antigen-related cell adhesion molecule 5 (CEACAM5) NM_004363 | ++ | ND | ND | ++ | ND | ND | |
| Collagen type XVIII (Endostatin) AF018081 | ++ | ND | ND | +/− | ND | ND | |
| Collagen type 1 alpha 1 (Col1A1) NM_000088 | ++ | ND | ND | + | ND | ND | |
| Collagen type IV alpha 2 (Col4A2) X05610 | ++ | ND | ND | + | ND | ND | |
| Cystatin C (amyloid angiopathy and cerebral hemorrhage, CST3) NM_000099 | ++ | ND | ND | + | ND | ND | |
| Catenin, Cadherin associated protein, alpha 1 (CTNNA1) NM_001903 | ++ | ND | ND | + | ND | ND | |
| Catenin, Cadherin associated protein, Beta 1 (CTNNB1) NM_001904 | ++ | ND | ND | + | ND | ND | |
| Catenin, Cadherin associated protein, delta 1 (CTNND1) AF062343 | ++ | ND | ND | ++ | ND | ND | |
| Cathepsin B (CTSB) L16510 | ++ | ND | ND | + | ND | ND | |
| Cathepsin D lysosomal aspartyl protease (CTSD) M11233 | + | ND | ND | − | ND | ND | |
| Cathepsin L (CTSL) X12451 | ++ | ND | ND | + | ND | ND | |
| Fibronectin 1 (FN1) X02761 | +++ | ND | ND | +++ | ND | ND | |
| Integrin alpha 5, fibronectin receptor (ITGA5) X06256 | +++ | ND | ND | −/+ | ND | ND | |
| Integrin alpha 6, laminin receptor (ITGA6) X53586 | −/+ | ND | ND | − | ND | ND | |
| Integrin alpha V, vitronectin receptor (ITGAV) NM_002210 | +++ | ND | ND | +++ | ND | ND | |
| Integrin beta 1, fibronectin receptor (ITGB1) NM_002211 | +++ | ND | ND | +++ | ND | ND | |
| Integrin beta 5, (ITGB5) J05633 | +++ | ND | ND | +++ | ND | ND | |
| Laminin B1 chain (LAMB1) M61916 | +++ | ND | ND | +++ | ND | ND | |
| Laminin gamma 1 (LAMC1) Jo3202 | + | ND | ND | − | ND | ND | |
| Hyaluronidases, meningioma expressed antigen 5 (MGEA5) NM_012215 | +++ | ND | ND | + | ND | ND | |
| Matrix Metalloproteinase 1 (MMP1) X05231 | ++ | ND | ND | − | ND | ND | |
| Matrix Metalloproteinase 10 (MMP10) NM_002425 | ++ | ND | ND | − | ND | ND | |
| Stromelysin-3 (MMP11) X57766 | + | ND | ND | − | ND | ND | |
| Matrix Metalloproteinase 13 (MMP13) X75308 | + | ND | ND | − | ND | ND | |
| mRNA for membrane type matrix Metalloproteinase 1 (MMP14) D26512 | +++ | ND | ND | −/+ | ND | ND | |
| Matrix Metalloproteinase 15 membrane inserted (MMP15) D86331 | +++ | ND | ND | − | ND | ND | |
| Matrix Metalloproteinase 17 membrane inserted (MMP17) NM_016155 | + | ND | ND | − | ND | ND | |
| Matrix Metalloproteinase 2 (MMP2) J03210 | +++ | ND | ND | +++ | ND | ND | |
| Matrix Metalloproteinase 24 membrane inserted (MMP24) NM_006690 | +++ | ND | ND | −/+ | ND | ND | |
| mRNA matrix Metalloproteinase 26 (MMP26) AF291664 | +++ | ND | ND | +++ | ND | ND | |
| Matrix Metalloproteinase 3 (MMP3) X05232 | +++ | ND | ND | − | ND | ND | |
| Neurophil cell adhesion molecule (NRCAM) NM_005010 | + | ND | ND | − | ND | ND | |
| Plasminogen activator inhibitor type 1 (SERPINE1) M16006 | +++ | ND | ND | +++ | ND | ND | |
| Osteonectin, secreted protein acidic cystein-rich (SPARC) XM_003989 | +++ | ND | ND | +++ | ND | ND | |
| Osteopontin, secreted phosphoprotein 1 (SPP1) M83248 | +++ | ND | ND | +++ | ND | ND | |
| Thrombosponin 1 (THBS1) NM_003246 | +++ | ND | ND | +++ | ND | ND | |
| Tissue inhibitor of metalloproteinase 1 (TIMP1) NM_003254 | +++ | ND | ND | −/+ | ND | ND | |
| Tissue inhibitor of metalloproteinase 2 (TIMP2) NM_003255 | +++ | ND | ND | ++ | ND | ND | |
| Tissue inhibitor of metalloproteinase 3 (TIMP3) NM_000362 | ++ | ND | ND | −/+ | ND | ND | |

Table 7 summarizes the data accumulated following chip analysis of all LIF pathway related genes.

TABLE 7

| Gene | I series | | | J series | | | Confirmed by RT-PCR |
|---|---|---|---|---|---|---|---|
| | I6 | I3 | H9 | J6 | J2 | J3 | |
| BCL2-associated X protein (Bax) L22474 | + | ND | ND | + | ND | ND | |
| Cerebellin 1 precursor (CBLN1) NM_004352 | + | ND | ND | + | ND | ND | |
| Corticotropin releasing hormone (CRH) NM_000756 | + | ND | ND | + | ND | ND | |
| Corticotropin releasing hormone binding protein (CRHBP) NM_001882 | −/+ | ND | ND | + | ND | ND | |
| Corticotropin releasing hormone receptor 1 (CRHR1) NM_004382 | ++ | ND | ND | ++ | ND | ND | |
| Corticotropin releasing hormone receptor 2 (CRHR2) NM_001883 | ++ | ND | ND | +++ | ND | ND | |
| Chemokine receptor 4 (CXCR4) NM_003467 | + | ND | ND | + | ND | ND | |
| Prothrombin kringle-1 (F2) J00307 | + | ND | ND | + | ND | ND | |
| Basic fibroblast growth factor (FGF2) NM_002006 | −/+ | ND | ND | −/+ | ND | ND | |
| Fibroblast growth factor 9 (FGF9) XM_007105 | + | ND | ND | + | ND | ND | |
| Fibroblast growth factor receptor 1 (FGFR1) M34185 | + | ND | ND | + | ND | ND | + |
| Fusion derived from t(12; 16) malignant liposarcoma (FUS) NM_004960 | + | ND | ND | ++ | ND | ND | |
| Heat shock 27 KD protein (HSPB1) Z23090 | + | ND | ND | + | ND | ND | |
| Interleukin 6 (IL6) M14584 | − | ND | ND | −/+ | ND | ND | |
| Interleukin 6 signal transducer, gp130 oncostatin M receptor (gp130) NM_002184 | + | ND | ND | + | ND | ND | |
| v-jun avian sarcoma virus 17 oncogene homolog (v-jun) NM_002228 | ++ | ND | ND | +++ | ND | ND | |
| Leukemia inhibitory factor receptor mRNA (LIFR) NM_002310 | + | ND | ND | + | ND | ND | + |
| Leukemia inhibitory factor (LIF) X13967 | − | ND | ND | − | ND | ND | Was demonstrated with RT-PCR for J6 |
| Neurotrophin receptor-interacting MAGE homologue (MAGED1) NM_006986 | + | ND | ND | + | ND | ND | |
| Nerve growth factor beta polypeptide (NGFB) X52599 | + | ND | ND | + | ND | ND | |
| Neuropeptide Y receptor Y6 (NPY6R) NM_006173 | + | ND | ND | + | ND | ND | |
| Suc1-associated neurotrophic factor target 2 (FGFR signaling adaptor) (SNT-2) NM_006653 | + | ND | ND | + | ND | ND | |
| Signal transducer and activator of transcription 3 (STAT3) NM_003150 | −/+ | ND | ND | ++ | ND | ND | |
| Tumor protein P53 (p53) M14694 | −/+ | ND | ND | + | ND | ND | |
| Urocortin (UCN) NM_003353 | ++ | ND | ND | +++ | ND | ND | |

The difference between EBC and hESC gene expression could be the result of either the higher background differentiation of the EBCs compared to that of the hESCs, as mentioned earlier, or a significant difference between the two cell lines stemming from the different embryonic developmental stage. To explore the two possibilities, double staining for OCT4 and early mesodermal marker—Brachyury [Herrmann et al. 1990; Wilkinson et al. 1990; Herrmann 1991] was performed. It was hypothesized, that if the difference was due to background differentiation, then in some colonies only several EBCs would be positive for Brachyury and that these cells would be negative for OCT4. A double expression of the two markers would indicate that the second possibility is more likely to be true. First, the expression of Brachyury was measured in undifferentiated cells by RT-PCR. Only line J6 expressed this gene in three separate samples, whereas J2 and J3 expressed it inconsistently. The hESCs did not express it in any of the examined nine samples from three different lines. No double staining was found in undifferentiated colonies of the hESC line I3. It was found that almost all the cells were positive for OCT4 and few were positive for Brachyury (FIGS. 9A-I). However, when undifferentiated colonies of the line J6 were examined, most of the cells were double stained (FIGS. 10A-I).

Figure 11A:
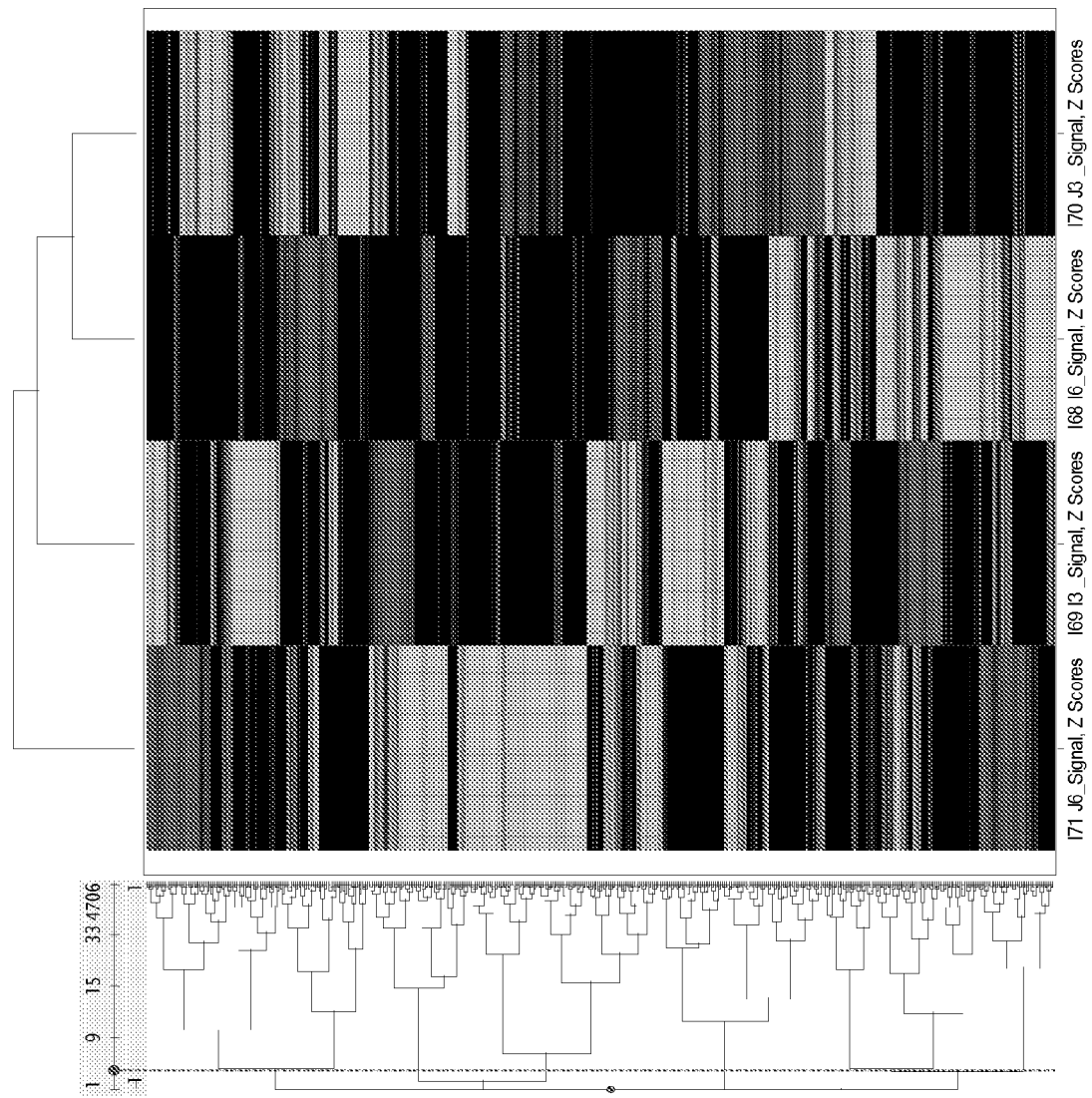
FIGS. 11A-B are computer generated images following bioinformatic analysis using the MAS 5.0 Affymetrix array analysis software of four Affymetric focus gene chips hybridized with cDNA from four cell lines (I3, I6 J3 and J6).
Figure 11B:
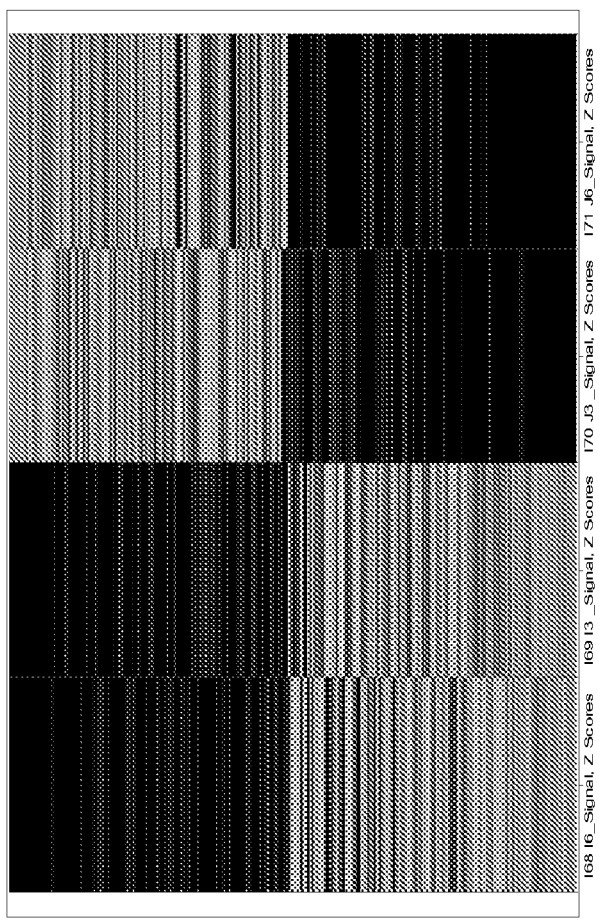

The gene profiles of undifferentiated hES cells from lines I3 and I6, and undifferentiated EB cells from lines J3 and J6 were compared using Affymetrix focused DNA chips (Affymetrix U133A GeneChip DNA microarray). Clustering analysis of the four lines showed a distinct expression (FIGS. 11A-B). Lines I3 and I6 exhibited a significantly higher number of "present" calls (According to the MAS5 method of analysis, "present" call genes are those whose 11 representative expression spots averaged a score higher than 30) than J3 and J6. No differences were found between the number of "present" calls of I3 compared with I6, or J3 compared with J6, although some individual gene expression signals were found to be different. This finding is consistent with other reports demonstrating that embryonic stem cells express a higher number of genes compared with other progenitors (such as hematopoietic stem cells or skin stem cells); these genes "switch off" during the differentiation process [Mashiach et al, 2005, FASEB 19:147-9]. The signal intensities of lines J3 and J6, however, were found to be higher than the signal intensities produced by the hESC lines. A list of 238 genes in lines J3 and J6 was found to be significantly different (either increased or decreased three fold) than the average expression of I3 and I6 as examined by t-test. The gene list also includes the early mesodermal marker Brachyury, further corroborating both the RT-PCR results and the double staining with Oct 4. Go-chart analysis of these 238 genes revealed that the majority of these genes are related to cell growth, cell maintenance, metabolism of proteins and nucleic acid and signal transduction pathways (FIG. 12). The signal transduction genes include 4 genes from the WNT signaling pathway, which were found to be decreased in line J3 and J6.

To allow an even wider comparison between the two cell types, illumine bead array analysis was performed using an array of 24,364 genes. The results are summarized in Table 8 below (J3-cells of the present invention; hES-human embryonic stem cells; Shh—Chip control; sd—standard deviation; av—average). It was found that 2498 of them showed a 5 fold change in expression level. Of these, only 696 genes (27%) were expressed at a higher level (greater than 5 fold) in the stem cells of the present invention. The average expression level of those 696 genes was much lower than the average expression level of those genes where expression was higher in ESCs than the stem cells of the present invention. The same result appears when expression changes by at least 15 fold is examined; 1354 genes are expressed in the HESC while only 411 (30%) in the DBC cells.

Lengthy table referenced here

US08354277-20130115-T00001

Please refer to the end of the specification for access instructions.

Using two-dimensional gel electrophoresis, extracted proteins from undifferentiated cells, and 5-day-old EBs from I6, I4, J3 and J6 lines were compared. Clear differences were found between the treatments (FIGS. 13A-B). More differences were found between the EBs derived from EBCs compared with corresponding undifferentiated EBCs than the EBs derived from hESCs compared with corresponding undifferentiated ESCs. These differences include both protein appearance and post translational differences such as phosphorylation.

Directed differentiation into osteoblasts was also tested. These experiments revealed higher staining of calcium in EBs derived from EBCs compared with EBs derived from hESCs. Examples are illustrated in FIG. 14.

Conclusions

Like hESCs, EBCs sustain a normal karyotype, express most of the typical ES cell surface markers, are capable of undifferentiated prolonged proliferation and demonstrate the ability to differentiate into the three embryonic germ layers progeny. On the other hand, EBCs hold a significantly different genetic signature, including expressing early mesodermal markers at the undifferentiated stage, demonstrating a tendency to differentiate into mesodermal tissues, having an altered expression profile, having a lower tendency to form teratomas, having an altered single cell and colony morphology, and having a reduced pluripotency in comparison with hESCs.

It appears that EBCs represent a distinct cell-population related to early stage of embryonic development, as compared to hESCs.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

LENGTHY TABLES

The patent contains a lengthy table section. A copy of the table is available in electronic form from the USPTO web site (http://seqdata.uspto.gov/?pageRequest=docDetail&DocID=US08354277B2). An electronic copy of the table will also be available from the USPTO upon request and payment of the fee set forth in 37 CFR 1.19(b)(3).

What is claimed is:

1. An isolated primate embryonic cell line that exhibits for at least 20 passages an undifferentiated proliferative state, the ability to differentiate to derivatives of each of an endoderm, mesoderm, and ectoderm tissue and a double staining expression of brachyury and Octamer binding transcription factor 4 (OCT-4), but not of SSEA-1.

2. The isolated primate embryonic cell line of claim 1 further expressing at least one cartilage marker.

3. The isolated primate embryonic cell line of claim 2 wherein said at least one cartilage marker is selected from the group consisting of COMP, aggrecan and collagen type II.

4. A cell culture comprising the isolated primate embryonic cell line of claim 1.

5. The cell culture of claim 4, further comprising feeder cells.

6. The cell culture of claim 4, further comprising growth medium.

7. A method of generating a primate embryonic cell culture comprising;
   (a) providing a pre-implantation stage blastocyst;
   (b) ex vivo culturing said pre-implantation stage blastocyst on fibroblast feeder cells or on a synthetic extracellular matrix for at least nine days to fourteen days post fertilization to produce a pre-gastrulation, extended blastocyst;
   (c) isolating cells from said extended blastocyst; and
   (d) culturing said isolated extended blastocyst cells on fibroblast feeder cells, an extracellular matrix or media comprising basic fibroblast growth factor, thereby generating a primate embryonic cell culture comprising embryonic cells that express brachyury and Oct-4, are maintained in an undifferentiated proliferative states for at least 20 passages and have the capability to develop in to each of the three germ layers: endoderm, mesoderm and ectoderm.

8. A method of generating a primate embryonic cell line comprising;
   (a) providing a pre-implantation stage blastocyst;
   (b) ex vivo culturing said pre-implantation stage blastocyst on fibroblast feeder cells or on a synthetic extracellular matrix for at least nine days to fourteen days post fertilization to produce an extended blastocyst
   (c) isolating cells from said extended blastocyst;
   (d) culturing said isolated extended blastocyst cells on fibroblast feeder cells, an extracellular matrix or media comprising basic fibroblast growth factor; and
   (d) cloning at least one of said isolated cells, thereby generating a primate embryonic cell line comprising embryonic cells that express brachyury and Oct-4, are maintained in an undifferentiated proliferative state for at least 20 passages and have the capability to develop in to each of the three germ layers: endoderm, mesoderm and ectoderm.

9. A pharmaceutical composition comprising as an active ingredient the isolated primate embryonic cell line of claim 1 and a pharmaceutically acceptable carrier.

10. The isolated primate embryonic cell line of claim 1, maintaining a stable normal karyotype for at least one year.

11. The isolated primate embryonic cell line of claim 1, expressing SSEA4 and TRA-1-60 markers.

12. The isolated primate embryonic cell line of claim 1, expressing less TRA-1-81 marker than an embryonic stem cell of the same primate species not expressing brachyury using identical assay conditions.

13. The isolated primate embryonic cell line of claim 1, capable of colony organization of columnar epithelium with villi throughout the upper side of said colony.

14. The isolated primate embryonic cell line of claim 1, having an OCT4 protein level lower than the OCT4 protein level in an embryonic stem cell of the same primate species not expressing brachyury using identical assay conditions.

15. The isolated primate embryonic cell line of claim 1, expressing more mesodermal differentiating markers than an embryonic stem cell of an identical primate not expressing brachyury using identical assay conditions.

16. The isolated primate embryonic cell line of claim 1, being genetically modified.

17. The method of claim 7, wherein said fibroblast feeder cells are mouse fibroblast feeder cells or human fibroblast feeder cells.

18. The method of claim 17, wherein said mouse fibroblast feeder cells are mitotically inactivated mouse embryonic fibroblasts or primary mouse embryonic fibroblasts.

19. The method of claim 17, wherein said human fibroblast feeder cells are selected from the group comprising embryonic fibroblast cells, adult fallopian epithelial cells and foreskin cells.

20. The isolated primate embryonic stem cell line of claim 1 being in an undifferentiated proliferative state for at least 100 passages.

21. The isolated primate embryonic cell line of claim 1 being immortalized.

22. The isolated primate embryonic cell line of claim 1, wherein the primate is a human.

23. The method of claim 7, wherein said blastocyst is a human blastocyst.

24. The method of claim 8, wherein said blastocyst is a human blastocyst.

25. An isolated primate embryonic cell line generated according to the method of claim 7 and comprising cells that exhibit for at least 20 passages an undifferentiated proliferative state, the ability to differentiate to derivatives of each of an endoderm, mesoderm, and ectoderm tissue and a double staining expression of brachyury and Octamer binding transcription factor 4 (OCT-4), but not of SSEA-1.

26. An isolated primate embryonic cell line generated according to the method of claim 7, and comprising cells that exhibit for at least 20 passages an undifferentiated proliferative state, the ability to differentiate to derivatives of each of an endoderm, mesoderm, and ectoderm tissue and a double staining expression of fibroblast growth factor 5 (FGF5) and Octamer binding transcription factor 4 (OCT-4), but not of SSEA-1.

27. An isolated clonal primate embryonic cell line generated according to the method of claim 8, and comprising cells that exhibit for at least 20 passages an undifferentiated proliferative state, the ability to differentiate to derivatives of each of an endoderm, mesoderm, and ectoderm tissue and a double staining expression of brachyury and Octamer binding transcription factor 4 (OCT-4), but not of SSEA-1.

28. An isolated clonal primate embryonic cell line generated according to the method of claim 8, and comprising cells that exhibit for at least 20 passages an undifferentiated proliferative state, the ability to differentiate to derivatives of each of an endoderm, mesoderm, and ectoderm tissue and a double staining expression of fibroblast growth factor 5 (FGF5) and Octamer binding transcription factor 4 (OCT-4), but not of SSEA-1.

29. An isolated clonal primate embryonic cell line comprising cells that exhibit for at least 20 passages an undifferentiated proliferative state, the ability to differentiate to derivatives of each of an endoderm, mesoderm, and ectoderm tissue and a double staining expression of brachyury and Octamer binding transcription factor 4 (OCT-4), but not of SSEA-1.

30. An isolated primate embryonic cell line that exhibits for at least 20 passages an undifferentiated proliferative state, the ability to differentiate to derivatives of each of an endoderm, mesoderm, and ectoderm tissue and a double staining expression of brachyury and Octamer binding transcription factor 4 (OCT-4), but not of SSEA-1, wherein the cell line is not genetically modified.

31. The isolated primate embryonic cell line of claim 1, wherein the cell line exhibits staining expression of SRY-related HMG-box-2 (SOX2) and Nanog.

32. The isolated primate embryonic cell line of claim 25, wherein the cell line exhibits staining expression of SRY-related HMG-box-2 (SOX2) and Nanog.

33. The isolated primate embryonic cell line of claim 26, wherein the cell line exhibits staining expression of SRY-related HMG-box-2 (SOX2) and Nanog.

34. The isolated clonal primate embryonic cell line of claim 27, wherein the cell line exhibits staining expression of SRY-related HMG-box-2 (SOX2) and Nanog.

35. The isolated clonal primate embryonic cell line of claim 28, wherein the cell line exhibits staining expression of SRY-related HMG-box-2 (SOX2) and Nanog.

36. The isolated clonal primate embryonic cell line of claim 29, wherein the cell line exhibits staining expression of SRY-related HMG-box-2 (SOX2) and Nanog.

* * * * *

SEQUENCE LISTING

<160> NUMBER OF SEQ ID NOS: 80

<210> SEQ ID NO 1
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 1

```
cagtcgtcag cctgaacata acatcc                                         26

<210> SEQ ID NO 2
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 2
aggttgcact tgtccacgca ttccc                                          25

<210> SEQ ID NO 3
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 3
acacgggagt gcatctacta caacg                                          25

<210> SEQ ID NO 4
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 4
ttcatgagct gggccttcca gacac                                          25

<210> SEQ ID NO 5
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 5
gagaacaatg agaaccttca ggaga                                          25

<210> SEQ ID NO 6
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 6
ttctggcgcc ggttacagaa cca                                            23

<210> SEQ ID NO 7
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 7
actaacatga gtgtggatcc                                                20

<210> SEQ ID NO 8
<211> LENGTH: 20
<212> TYPE: DNA
<213> ORGANISM: Artificial sequence
```

```
<220> FEATURE:
<223> OTHER INFORMATION: Single strand DNA oligonucleotide

<400> SEQUENCE: 8
tcatcttcac acgtcttcag                                                      20

<210> SEQ ID NO 9
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 9
cagcatcact gaatcacaga gc                                                   22

<210> SEQ ID NO 10
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 10
agtatgaaac atccccacag gg                                                   22

<210> SEQ ID NO 11
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 11
caaaagagtg tctgtgag                                                        18

<210> SEQ ID NO 12
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 12
ccatgtattt acattggc                                                        18

<210> SEQ ID NO 13
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 13
gcgtacgcaa attaaagtcc aga                                                  23

<210> SEQ ID NO 14
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 14
cagcatccta aacagctcgc agaat                                                25
```

```
<210> SEQ ID NO 15
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 15
ctacaacgcc tacgagtcct aca                                                23

<210> SEQ ID NO 16
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 16
gttgcaccag aaaagtcaga gttg                                               24

<210> SEQ ID NO 17
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 17
cactgatagg aaccctagag g                                                  21

<210> SEQ ID NO 18
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 18
ctccgactgc ttgaatcttg g                                                  21

<210> SEQ ID NO 19
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 19
cccccggcgg caatagca                                                      18

<210> SEQ ID NO 20
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 20
tcggcgccgg ggagatacat                                                    20

<210> SEQ ID NO 21
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 21
```
atctggcacc acaccttcta caatgagctg cg                    32

<210> SEQ ID NO 22
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 22
cgtcatactc ctgcttgctg atccacatct gc                    32

<210> SEQ ID NO 23
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 23
agcagcagtt ctgaagagat agtgcc                           26

<210> SEQ ID NO 24
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 24
gtggagagtt cactgaactt gtccc                            25

<210> SEQ ID NO 25
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 25
agcatcataa tggactctgt ggtgcc                           26

<210> SEQ ID NO 26
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 26
agtccgatag agttacccgc caagc                            25

<210> SEQ ID NO 27
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 27
tctgcagcta ggtcctctca tcagc                            25

<210> SEQ ID NO 28
<211> LENGTH: 25
<212> TYPE: DNA
<213> ORGANISM: Artificial sequence

```
<220> FEATURE:
<223> OTHER INFORMATION: Single strand DNA oligonucleotide

<400> SEQUENCE: 28
tatactgctc catatcgacc tcggc                                            25

<210> SEQ ID NO 29
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 29
agaaattcat caggctgtga agcgcg                                           26

<210> SEQ ID NO 30
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 30
ttcctccgat cgcacacatt tgtcg                                            25

<210> SEQ ID NO 31
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 31
tgttctcctg ccaggacaag cagaac                                           26

<210> SEQ ID NO 32
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 32
tcttgaaggc tatgtaggcc acaagg                                           26

<210> SEQ ID NO 33
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 33
tagtcactga caacaacggt gcagtc                                           26

<210> SEQ ID NO 34
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 34
acagtgctcg ctgaactcca tgagc                                            25
```

```
<210> SEQ ID NO 35
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 35
acctgactcc tgaggagaag tctgc                                          25

<210> SEQ ID NO 36
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 36
tagccacacc agccaccact ttctg                                          25

<210> SEQ ID NO 37
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 37
cgatggctgc acgagtcaca c                                              21

<210> SEQ ID NO 38
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 38
caggttggga tggagggagt ttac                                           24

<210> SEQ ID NO 39
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 39
ccgggcagag ggcaatagca ggtt                                           24

<210> SEQ ID NO 40
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 40
caatgatggg gaggcgtgag                                                20

<210> SEQ ID NO 41
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 41
```

```
gggtggccgc tgggggtct t                                          21

<210> SEQ ID NO 42
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 42
cttgccgcag ctgatgggtc tc                                        22

<210> SEQ ID NO 43
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 43
gcgtccgcta ccccatctct a                                         21

<210> SEQ ID NO 44
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 44
gcgctctaag ggcacattca gtt                                       23

<210> SEQ ID NO 45
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 45
ccagtgcaca gagggtttg                                            20

<210> SEQ ID NO 46
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 46
tccgagggtg ccgtgag                                              17

<210> SEQ ID NO 47
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 47
taaggtggat cttcaggtag c                                         21

<210> SEQ ID NO 48
<211> LENGTH: 21
<212> TYPE: DNA
<213> ORGANISM: Artificial sequence
```

```
<220> FEATURE:
<223> OTHER INFORMATION: Single strand DNA oligonucleotide

<400> SEQUENCE: 48
catctcattg gtgagctccc t                                              21

<210> SEQ ID NO 49
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 49
tctatgaggg ctacgctttg                                                20

<210> SEQ ID NO 50
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 50
cctgactgga aggtagatgg                                                20

<210> SEQ ID NO 51
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 51
accatggtgc atctgactcc tgagg                                          25

<210> SEQ ID NO 52
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 52
acttgtgagc caaggcatta gccac                                          25

<210> SEQ ID NO 53
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 53
agtcgtcttt gacactggtt cgtcc                                          25

<210> SEQ ID NO 54
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 54
ggtagaacct gagatgtagg atgc                                           24
```

```
<210> SEQ ID NO 55
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 55
agacatcgca ctgactgaga ac                                              22

<210> SEQ ID NO 56
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 56
gacgggtcac tatctgtgca ac                                              22

<210> SEQ ID NO 57
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 57
atgaactcct tctccacaag cgc                                             23

<210> SEQ ID NO 58
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 58
gaagagccct caggctggac tg                                              22

<210> SEQ ID NO 59
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 59
tcaagccaaa cacaaacagc                                                 20

<210> SEQ ID NO 60
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 60
acgtctgaac aatggcatga                                                 20

<210> SEQ ID NO 61
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 61
```
gccggagggc aagcgtagc cctaag                                        26

<210> SEQ ID NO 62
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 62
ctgcctgatc tcagcggcac ccacatc                                      27

<210> SEQ ID NO 63
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 63
ccaacacctc ccactatgac                                              20

<210> SEQ ID NO 64
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 64
tatactcgcc cttcttgctg                                              20

<210> SEQ ID NO 65
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 65
gctgggctca gtattcccca aatac                                        25

<210> SEQ ID NO 66
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 66
gacgacaatc tctgacctga gtagg                                        25

<210> SEQ ID NO 67
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 67 agacccttg aagtcaagga caccg                                         25

<210> SEQ ID NO 68
<211> LENGTH: 25
<212> TYPE: DNA
<213> ORGANISM: Artificial sequence

```
<220> FEATURE:
<223> OTHER INFORMATION: Single strand DNA oligonucleotide

<400> SEQUENCE: 68
ccattgctga agaccttagt gatgc                                              25

<210> SEQ ID NO 69
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 69
cctttggcac aatgaagtgg gtaacc                                             26

<210> SEQ ID NO 70
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 70
cagcagtcag ccatttcacc atagg                                              25

<210> SEQ ID NO 71
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 71
ctcagtgatc ctgatcagat gaacg                                              25

<210> SEQ ID NO 72
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 72
agtccctggc ggcaagatta tcaag                                              25

<210> SEQ ID NO 73
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 73
gctggattgt ctgcaggatg gggaa                                              25

<210> SEQ ID NO 74
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 74 tccccctgaag aaaattggtt aaaat                                             25
```

```
<210> SEQ ID NO 75
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 75
tcaaaaactc ctagctggcc t                                              21

<210> SEQ ID NO 76
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 76
ctttccagag ctcctttcag gt                                             22

<210> SEQ ID NO 77
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 77
gcagctatct ttctggtcac at                                             22

<210> SEQ ID NO 78
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 78
actctgaggt gacgttcttt tg                                             22

<210> SEQ ID NO 79
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 79
tgaacacaga cgctatgcgc tcag                                           24

<210> SEQ ID NO 80
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 80
cacctttatg tgagtggaca cagag                                          25
```